United States Patent
Gavathiotis

(10) Patent No.: US 11,760,780 B2
(45) Date of Patent: Sep. 19, 2023

(54) TARGETING DIMERIZATION OF BAX TO MODULATE BAX ACTIVITY

(71) Applicant: ALBERT EINSTEIN COLLEGE OF MEDICINE, Bronx, NY (US)

(72) Inventor: Evripidis Gavathiotis, Flushing, NY (US)

(73) Assignee: Albert Einstein College of Medicine, Bronx, NY (US)

(*) Notice: Subject to any disclaimer, the term of this patent is extended or adjusted under 35 U.S.C. 154(b) by 0 days.

(21) Appl. No.: 16/357,364

(22) Filed: Mar. 19, 2019

(65) Prior Publication Data

US 2019/0202865 A1 Jul. 4, 2019

Related U.S. Application Data

(62) Division of application No. 15/311,861, filed as application No. PCT/US2015/032897 on May 28, 2015, now abandoned.

(Continued)

(51) Int. Cl.
  *C07K 14/00* (2006.01)
  *C07K 14/47* (2006.01)
  (Continued)

(52) U.S. Cl.
  CPC .............. *C07K 14/001* (2013.01); *C07K 7/06* (2013.01); *C07K 7/08* (2013.01); *C07K 14/00* (2013.01); *C07K 14/474* (2013.01); *G01N 33/502* (2013.01); *G01N 33/574* (2013.01); *G01N 33/68* (2013.01); *A61K 38/00* (2013.01);
  (Continued)

(58) Field of Classification Search
  CPC .......... A61K 38/00; A61P 35/00; A61P 43/00; C07K 14/00; C07K 14/001; C07K 14/474; C07K 7/06; C07K 7/08; G01N 2333/4703; G01N 2500/02; G01N 2500/04; G01N 33/502; G01N 33/574; G01N 33/68

See application file for complete search history.

(56) References Cited

U.S. PATENT DOCUMENTS

| 6,245,885 B1 | 6/2001 | Shore |
| 6,858,396 B2 * | 2/2005 | Dix ........................ C07C 229/26 435/23 |

(Continued)

FOREIGN PATENT DOCUMENTS

| WO | 00/20446 A2 | 4/2000 |
| WO | 00/23083 A1 | 4/2000 |

(Continued)

OTHER PUBLICATIONS

Ausili et al., The interaction of the Bax C-terminal Domain with membranes is influenced by the presence of negatively charged phospholipids, Biochemica et Biophysica Acta, vol. 1788:1924-1932 (Jun. 13, 2009) (Year: 2009).*

(Continued)

*Primary Examiner* — Randall L Beane
(74) *Attorney, Agent, or Firm* — Fox Rothschild LLP

(57) ABSTRACT

Methods are provided for identifying an agent that directly modulates a Bcl-2-associated x-protein (BAX) by promoting or disrupting dimerization of the BAX. Agents that directly modulate BAX by affecting dimerization are also provided.

9 Claims, 20 Drawing Sheets

Specification includes a Sequence Listing.

Related U.S. Application Data

(60) Provisional application No. 62/005,013, filed on May 30, 2014.

(51) Int. Cl.
    *C07K 7/08*     (2006.01)
    *A61K 38/00*     (2006.01)
    *G01N 33/574*     (2006.01)
    *G01N 33/68*     (2006.01)
    *C07K 7/06*     (2006.01)
    *G01N 33/50*     (2006.01)

(52) U.S. Cl.
CPC . *G01N 2333/4703* (2013.01); *G01N 2500/02* (2013.01); *G01N 2500/04* (2013.01)

(56) References Cited

U.S. PATENT DOCUMENTS

| | | | |
|---|---|---|---|
| 8,921,323 B2 | 12/2014 | Walensky et al. | |
| 9,303,024 B2 | 4/2016 | Walensky et al. | |
| 10,000,478 B2 | 6/2018 | Walensky et al. | |
| 2003/0096367 A1 | 5/2003 | Korsmeyer | |
| 2005/0250680 A1* | 11/2005 | Walensky | A61P 5/24 514/18.9 |
| 2008/0139481 A1* | 6/2008 | Dix | A61P 7/10 424/85.2 |
| 2010/0286057 A1* | 11/2010 | Walensky | A61P 3/10 514/18.9 |
| 2011/0288006 A1* | 11/2011 | Yeaman | A01N 47/44 514/21.3 |
| 2013/0189784 A1* | 7/2013 | Shukla | A61K 47/646 435/375 |
| 2015/0335671 A1 | 11/2015 | Gavathiotis et al. | |
| 2016/0347807 A1* | 12/2016 | Lim | C07K 14/4746 |
| 2018/0244664 A1 | 8/2018 | Walensky et al. | |
| 2018/0251532 A1 | 9/2018 | Gavathiotis et al. | |

FOREIGN PATENT DOCUMENTS

| | | | |
|---|---|---|---|
| WO | 09/042237 A2 | 4/2009 | |
| WO | WO-2009042237 A2 * | 4/2009 | ............. A61P 25/00 |
| WO | 10/042225 A2 | 4/2010 | |
| WO | 11/103567 A2 | 8/2011 | |

OTHER PUBLICATIONS

Valero et al., μ-Calpain Conversion of Antiapoptotic Bfl-1 (BCL2A1) into a Prodeath Factor Reveals Two Distinct alpha-Helices Inducing Mitochondria-Mediated Apoptosis, PLOS One, 7(6): e38620. https://doi.org/10.1371/journal.pone.0038620 (Jun. 20, 2012) (Year: 2012).*

Wagner et al., New Naturally Occurring Amino Acids, Anew. Chem. Int. Ed. Engl. 22:816-828 (1983) (Year: 1983).*

Kosloff et al. (Sequence-similar, structure-dissimilar protein pairs in the PDB, Proteins, vol. 71:891-902 (2008) (Year: 2008).*

Kimple et al. (Overview of Affinity Tags for Protein Purification, Current Protocols in Protein Science 9.9.1-9.9.23, Aug. 2013, DOI: 10.1002/0471140864.ps0909s73 (2013) (Year: 2013).*

PCT International Search Report and Written Opinion, dated Nov. 19, 2015 in connection with PCT International Application No. PCT/US2015/32897, 13 pages.

Barclay L A et al., entitled "Inhibition of Pro-Apoptotic BAX by a Noncanonical Interaction Mechanism," Molecular Cell 57, 1-14, Mar. 5, 2015.

Braun C R et al., entitled "Photoreactive Stapled BH3 Peptides to Dissect the BCL-2 Family Interactome," Chem Biol., Dec. 22, 2010; 17(12): 1325-1333.

Gavathiotis E et al., entitled "Tracking BAX once its trigger is pulled," Cell Cycle 10:6 868-870, Mar. 15, 2011.

Gavathiotis E et al., entitled "BH3-Triggered Structural Reorganization Drives the Activation of Pro-apoptotic BAX," Mol Cell. Nov. 12, 2010; 40(3): 481-492.

Gavathiotis E et al., entitled "Direct and selective small-molecule activation of proapoptotic BAX," Nat Chem Biol., Jul. 2012; 8(7): 639-645.

Gavathiotis E et al., entitled "BAX Activation is Initiated at a Novel Interaction Site," Nature, Oct. 23, 2008; 455(7216): 1076-1081.

George N M et al., entitled "A three-helix homo-oligomerization domain containing BH3 and BH1 is responsible for the apoptotic activity of Bax," Genes Dev., 2007, 21: 1937-1948.

Hetz C et al., entitled "Bax Channel Inhibitors Prevent Mitochondrion-mediated Apoptosis and Protect Neurons in a Model of Global Brain Ischemia," The Journal of Biological Chemistry, vol. 280, No. 52, pp. 42960-42970, 2005.

Peixoto P M et al., entitled "MAC Inhibitors suppress mitochondrial apoptosis," Biochem J. (2009) 423, 381-387.

Walensky L D et al., entitled "BAX Unleashed: The Biochemical Transformation of an Inactive Cytosolic Monomer into a Toxic Mitochondrial Pore," Trends Biochem Sci., Dec. 2011; 36(12): 642-652.

Whelan R S et al., entitled "Bax regulates primary necrosis through mitochondrial dynamics," PNAS, Apr. 24, 2012, vol. 109, No. 17, 6566-6571.

GenBank: AAF82094.1, Bax Zeta [*Homo sapiens*], ncbi.nlm.gov, 2 pages (Jul. 6, 2000), also available at https://www.ncbi.nlnn.nih.gov/protein/AAF82094.1 (Year: 2000).

Robinson et al., (3-hairpin Peptidomimetics: Design, Structures, and Biological Activities, Accounts of Chemical Research, vol. 41(10):1278-1288 (ePub Apr. 16, 2008) (Year: 2008).

Hruby et al., Design of Peptide and Peptidomimetic Ligands with Novel Pharmacological Activity Profiles, Annu. Rev. Pharmacol. Toxicol., vol. 5:557-80 (2013) (Year: 2013).

Anderson, The Process of Structure-Based Drug Design, Chemistry & Biology, vol. 10:787-797 (Sep. 2003) (Year: 2003).

* cited by examiner

TARGETING DIMERIZATION OF BAX TO MODULATE BAX ACTIVITY

CROSS-REFERENCE TO RELATED APPLICATIONS

This application is a divisional of U.S. patent application Ser. No. 15/311,861, filed Nov. 17, 2016, which is a U.S. national stage entry under 35 U.S.C. § 371 of PCT International Patent Application No. PCT/US2015/032897, filed May 28, 2015, which claims the benefit of U.S. Provisional Patent Application No. 62/005,013, filed May 30, 2014, the contents of which are incorporated herein by reference into the subject application.

STATEMENT OF GOVERNMENT INTEREST

This invention was made with government support under grant number 5R00HL095929 awarded by the National Institutes of Health. The government has certain rights in this invention.

BACKGROUND OF THE INVENTION

Throughout this application various publications are referred to by number in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Programmed cell death, or apoptosis, is a fundamental process that regulates the critical balance between cellular life and death (1). Dysregulation of apoptosis results in an imbalance of normal homeostasis contributing to diseases such as cancer and neurodegeneration (2,3). The dysregulation of apoptosis is pivotal to a number of high mortality human diseases including cancer, cardiovascular diseases, and neurodegenerative diseases. The BCL-2 family of proteins comprises a complex interaction network that regulates the commitment of the cell to apoptosis at the mitochondrial pathway (4,5). The BCL-2 family includes both pro- and anti-apoptotic proteins. The pro-apoptotic BCL-2 proteins—BCL-2-associated X-protein (BAX) and BCL-2 homologous Antagonist Killer (BAK)—induce mitochondrial outer-membrane permeabilization and represent the key gatekeepers and effectors of mitochondrial apoptosis. Thus, inhibition of pro-apoptotic BAX or BAK impairs the cells' ability to initiate premature or unwanted cell death in terminally differentiated cells, including cardiomyocytes and neurons. Furthermore, activation of BAX or BAK promotes apoptosis and can overcome the resistance and blockades of tumor cells to undergo cell death.

Pro-apoptotic BAX is a critical effector member of the BCL-2 family (4,5) that is predominantly in the cytosol of nonapoptotic cells (6). Upon activation, BAX translocates from the cytosol to the mitochondria to execute permeabilization of the outer mitochondrial membrane and release of apoptogens into the cytosol (7,8), the "point of no return" for mitochondrial dysfunction and apoptosis (9,10).

Pro-apoptotic BAX is a highly regulated protein that interacts with pro- and anti-apoptotic BCL-2 proteins that trigger or inhibit its activation. Anti-apoptotic BCL-2 proteins such as BCL-2 and BCL-$X_L$ directly inhibit activated BAX whereas a subgroup of pro-apoptotic BCL-2 proteins, such as BIM and BID, use their BH3 domain to directly trigger BAX activation. The cytosolic conformation of BAX has a BH3 trigger site located at the N-terminal surface of its structure. The interaction of BAX with a stapled BIM BH3 helix, through the N-terminal trigger site (helices $\alpha 1/\alpha 6$), results in BAX activation involving a series of conformational changes. These conformational changes include the displacement of the $\alpha 1$-$\alpha 2$ loop from its closed to an open conformation and the mobilization of the $\alpha 2$ (BH3 domain) and $\alpha 9$ helices from the hydrophobic core to allow mitochondrial translocation and oligomerization, leading to mitochondrial permeabilization.

Despite remarkable progress in understanding BAX activation, current knowledge about the regulation mechanisms of BAX is limited. It is only understood how activated BAX is inhibited through the interaction of the BAX BH3 domain with the BH3 groove of the anti-apoptotic BCL-2 proteins. However, numerous proteins inhibiting cytosolic BAX have already been reported and posttranslational modifications have been studied which stabilize the cytosolic form of BAX. Emerging data suggest that BAX has a highly dynamic localization between cytosolic and mitochondrial compartments without requiring BAX activation. However, there is no structural evidence or any mechanistic understanding of how cytosolic BAX is kept under control. Current knowledge is limited to the structure of intact BAX, the NMR structure of which suggested that its $\alpha 9$ conformation keeps the protein in an inactive cytosolic form preventing it from translocation to the mitochondrial membrane.

Recent studies reported, in addition to the activation site at the N-terminal surface of full-length BAX structure, a second activation site that is revealed in the truncated structure, missing the C-terminal helix $\alpha 9$, which likely mimics the mitochondrial-attached form of BAX (11-14). Although the early steps of BAX activation have been established, there is still a lack of understanding of the mechanisms that keep BAX under control in the cytosol and regulate its activation and translocation to the outer mitochondrial membrane. Moreover, the conformations that BAX adopts in the cytosol and in the process of activation are critical for understanding BAX-mediated apoptosis and how BAX can be pharmacologically targeted. Therefore, BAX and proteins that regulate BAX activation, including other BCL-2 family members, are targets of intense investigation and drug discovery campaigns for the development of novel therapies (15,16).

Cell death modulation through BAX could have a therapeutic benefit in a number of diseases. Diseases associated with premature or unwanted cell death and characterized by abnormal activation, or expression or function of BAX include: cardiovascular diseases and disorders (e.g., arteriosclerosis, heart failure, heart transplantation, aneurism, chronic pulmonary disease, ischemic heart disease, hypertension, thrombosis, cardiomyopathies), neurodegenerative diseases and neurological disorders (e.g., Alzheimer's disease, Parkinson's disease, Huntington's disease, retinitis pigmentosa, spinal muscular atrophy, various forms of cerebellar degeneration, amyotrophic lateral sclerosis), immunological disorders (e.g., organ transplant rejection, arthritis, lupus, inflammatory bowel disease, Crohn's disease, asthma, multiple sclerosis, diabetes), ischemia (e.g., stroke, myocardial infarction and reperfusion injury), infertility (e.g., premature menopause, ovarian failure or follicular atresia), blood disorders (e.g., Fanconi anemia, aplastic anemia, thalassemia, congenital neutropenia, myelodysplasia), renal hypoxia, hepatitis, asthma and AIDS. However, there are currently no small molecule therapies that prevent or activate cell death through direct modulation of BAX's activity. There are inhibitors of the apoptotic pathway such as caspase inhibitors that prevent cell death in variety of cells. However, caspase inhibitors lack specificity among different caspases available in the cell, which is a liability for their successful clinical application. Direct activators of BAX may be particularly applicable in the treatment of cancer and could selectively overcome anti-apoptotic resistance of cancer cells and spare normal cells. Likewise, direct activators of BAX can be applied to promote apoptosis in autoimmune disease that are associated with uncontrolled production of immune cells. BAX inhibitors may be particularly applicable to heart disease, CNS disorder diseases and diseases of the liver and kidney where cell death is abnormally excessive.

The present invention addressed the need for identifying inhibitors and activators of BAX for therapeutic treatments.

SUMMARY OF THE INVENTION

The present invention discloses assays for identifying agents that interfere with or promote dimerization of BAX, and/or bind to previously unidentified dimer binding sites of BAX. The invention also provides for agents that promote or interfere with dimerization.

Methods are provided for identifying an agent as a candidate agent for promoting or inhibiting cell death comprising (a) contacting the agent with BCL-2-associated X-protein (BAX) monomers or portions thereof, and/or with BAX dimers, and (b) measuring if the agent inhibits or promotes dimerization of BAX; wherein a decrease in binding of BAX monomers to other BAX monomers or to portions of BAX monomers in the presence of the agent compared to in the absence of the agent indicates the agent inhibits dimerization of BAX, wherein an agent that agent inhibits dimerization of BAX is a candidate agent for promoting cell death; and wherein an increase in binding of BAX monomers or portions thereof to other BAX monomers or portions thereof in the presence of the agent compared to in the absence of the agent indicates that the agent promotes dimerization of BAX, wherein an agent that agent promotes dimerization of BAX is a candidate agent for inhibiting cell death.

Methods are also provided for identifying an agent that modulates the activity of BAX comprising contacting α9 helix peptide of BAX with N-terminal binding site of BAX in the presence of the agent and in the absence of the agent; and measuring binding between the α9 helix peptide of BAX and the N-terminal binding site of BAX, wherein decreased binding in the presence of the agent compared to binding in the absence of the agent indicates that the agent is a modulator of the activity of BAX.

Peptides are provided consisting of:

a)
(SEQ ID NO: 11)
TWQTVTIFVAGVLTASLTIWKKMG, b)
(SEQ ID NO: 12)
TWQTVTIFVAGVLTASLT, c)
(SEQ ID NO: 13)
TWQTVTIFVAGVLTA, d)
(SEQ ID NO: 14)
TWQTVTIFVAGVL, e) 11-30 amino acid residues comprising the sequence TXQTXXIFXAG (SEQ ID NO:15), where X at any position can independently be any amino acid, or natural or unnatural chemically modified amino acid, f) 15-30 amino acid residues comprising the sequence TXQTXXIFXAGVXTA (SEQ ID NO:16), where X at any position can independently be any amino acid, or natural or unnatural chemically modified amino acid, or g) 11-30 amino acid residues comprising the sequence Y1XY2Y3XXY4Y5XY6Y7 (SEQ ID NO:17), where Y1 is threonine or a conserved amino acid, or unnatural amino acid, Y2 is glutamine or a conserved residue or unnatural amino acid, where Y3 is threonine or a conserved amino acid, or unnatural amino acid, where Y4 is isoleucine or a conserved amino acid, or unnatural amino acid, where Y5 is phenylalanine or a conserved amino acid, or unnatural amino acid, where Y6 is alanine or a conserved amino acid, or unnatural amino acid, where Y7 is glycine or a conserved amino acid, or unnatural amino acid, where X at any position can independently be any amino acid, or natural or unnatural chemically modified amino acid.

Methods are provided for modulating BAX and for treating diseases and disorders associated with blockade or unwanted cell death and characterized by abnormal activation, expression or function of BAX comprising contacting BAX with the any of the peptides disclosed herein.

DETAILED DESCRIPTION OF THE INVENTION

A method is provided for identifying an agent as a candidate agent for promoting or inhibiting cell death comprising (a) contacting the agent with BCL-2-associated X-protein (BAX) monomers or portions thereof, and/or with BAX dimers, and (b) measuring if the agent inhibits or promotes dimerization of BAX;

wherein a decrease in binding of BAX monomers to other BAX monomers or to portions of BAX monomers in the presence of the agent compared to in the absence of the agent indicates the agent inhibits dimerization of BAX, wherein an agent that agent inhibits dimerization of BAX is a candidate agent for promoting cell death; and wherein an increase in binding of BAX monomers or portions thereof to other BAX monomers or portions thereof in the presence of the agent compared to in the absence of the agent indicates that the agent promotes dimerization of BAX, wherein an agent that agent promotes dimerization of BAX is a candidate agent for inhibiting cell death.

The agent can bind to amino acid residues of the N-terminal binding site and/or C-terminal binding site of BAX. For example, the agent can bind to the N-terminal of BAX at one or more of binding site residues S16, E17, Q18, 119, M20, K21, T22, G23, A24, L25, L26, 127, Q28, G29, F30, 131, Q32, D33, R34, A35, G36, R37, M38, G39, G40, E41, 131, Q32, D33, R34, A35, G36, R37, M38, G39, G40, E41, A42, P43, E44, L45, A46, L47, D48, P49, V50, P51, Q52, D53, A54, V129, P130, E131, L132, 1133, R134, T135, 1136, M137, G138, W139, T140, L141, D142, F143, L144, R145, E146, and R147. Alternatively, or in addition, the agent can bind to the C-terminal of BAX at one or more of binding site residues N73, M74, E75, L76, D98, M99, F100, 5101, D102, G103, N104, F105, N106, W107, G108, R109, 1152, Q153, D154, Q155, G156, G157, W158, D159, G160, L161, L162, 5163, Y164, F165, G166, T167, P168, T169, W170, Q171, T172, V173, T174, 1175, F176, V177, A178, G179, V180, L181, T182, A183, 5184, L185, T186, 1187, W188, K189 K190, M191, and G192.

In any of the methods disclosed herein, measurement of BAX as a dimer or monomer is carried out using one or more of a fluorescent polarization assay, size exclusion chromatography (SEC), polyacrylamide gel electrophoresis, dynamic light scattering, and an antibody that specifically binds to either BAX dimer or BAX monomer.

A method is also provided for identifying an agent that modulates the activity of BAX comprising contacting α9 helix peptide of BAX with N-terminal binding site of BAX in the presence of the agent and in the absence of the agent; and measuring binding between the α9 helix peptide of BAX and the N-terminal binding site of BAX, wherein decreased binding in the presence of the agent compared to binding in the absence of the agent indicates that the agent is a modulator of the activity of BAX.

In one embodiment, the agent is an inhibitor of BAX. Alternatively, the agent may be an activator of BAX.

Figure 15:
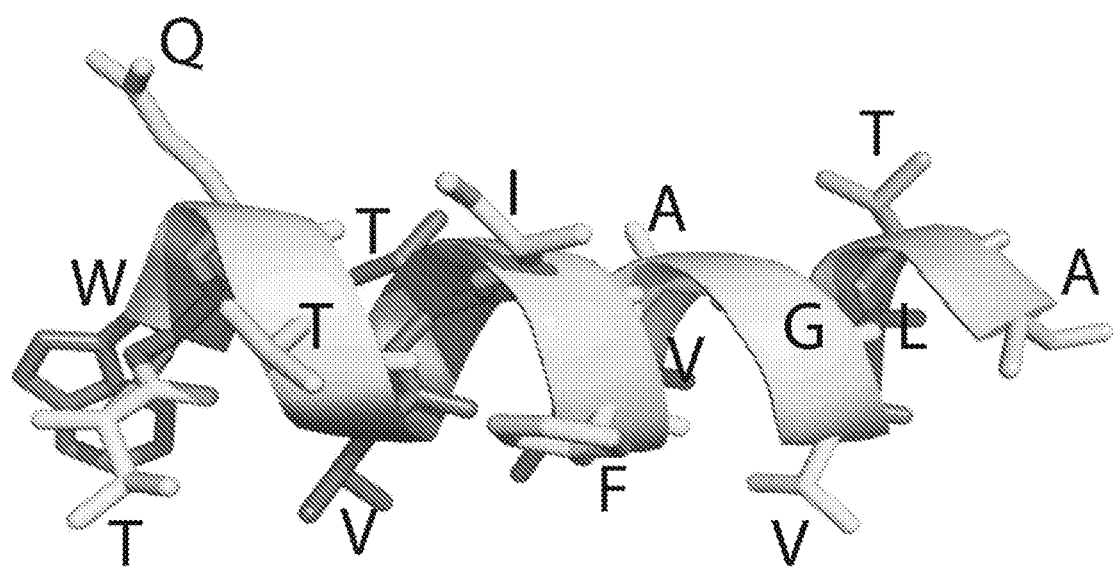
FIG. 15. Structure of the α9 helix peptide with labeled residues that interact with N-terminal binding site of BAX.

The α9 peptide of BAX has the amino acid sequence TWQTVTIFVAGVLTASLTIWKKMG (SEQ ID NO:11). The α9 helix peptide of BAX is illustrated in FIG. 15. In different embodiments, the α9 helix peptide of BAX or the N-terminal binding site of BAX can be immobilized on a solid substrate. Binding between the α9 helix peptide of BAX and the N-terminal binding site of BAX can be measured, for example, using a fluorescence assay or a surface plasmon resonance assay or a co-immunoprecipitation assay or an NMR assay.

Methods are also disclosed for identifying an agent as a modulator of a BCL-2-associated X-protein (BAX) comprising contacting the agent with the BAX and measuring if the agent inhibits or promotes the dimerization of BAX with another BAX or portion thereof, wherein a decrease in binding in the presence of the agent compared to in the absence of the agent indicates that the agent inhibits dimerization of BAX and an increase in binding of BAX to another BAX molecule in the presence of the agent compared to the absence of the agent indicates that the agent promotes dimerization of BAX.

In any of the methods disclosed herein, the BAX can be a human BAX.

The agent can be, for example, a small molecule, an isolated peptide, a synthetic peptide, a peptide-based agent with natural or non-natural amino acids or combinations, a hydrocarbon stapled peptide, a constrained peptide, a macrocycle, a peptoid, a peptidomimetic, a foldamer, an aptamer, an antibody, a monobody, a nanobody, or combinations thereof. In an embodiment, an agent is a peptidomimetic of the α9 helix of BAX.

In an embodiment of the methods described herein, the agent is a small molecule of 2000 daltons or less. In an embodiment of the methods described herein, the agent is a small molecule of 1500 daltons or less. In an embodiment of the methods described herein, the agent is a small molecule of 1000 daltons or less. In an embodiment of the methods described herein, the agent is a small molecule of 800 daltons or less. In an embodiment of the methods described herein, the agent is a small molecule of either 2000, 1500, 1000, 800, 700, 600, 500 or 400 daltons or less. In an embodiment of the methods described herein, the agent is a small organic molecule.

The methods disclosed herein can further comprise administering an agent identified as promoting dimerization of BAX or as inhibiting BAX to a subject with a disease or disorder associated with premature or unwanted cell death and characterized by abnormal activation, expression or function of BAX, and testing the efficacy of the agent in treating the disease. The methods can further comprise administering an agent identified as inhibiting dimerization of BAX or as activating BAX to a subject with a cancer and testing the efficacy of the agent in treating cancer.

Also provided are the following peptides that interact with the N-terminal binding site of BAX:

```
                                          (SEQ ID NO: 11)
1. TWQTVTIFVAGVLTASLTIWKKMG (corresponds to α9 of BAX)

(SEQ ID NO: 12)
2. TWQTVTIFVAGVLTASLT (SEQ ID NO: 13)
3. TWQTVTIFVAGVLTA (SEQ ID NO: 14)
4. TWQTVTIFVAGVL.
```

Highlighted amino acid residues interact with the N-terminal binding site of BAX. Other residues that do not interact with the N-terminal binding site of BAX can be mutated to any residue but the peptide sequences can still have binding and inhibitory function. Accordingly, the invention provides a peptide of 11-30 amino acid residues comprising the sequence: TXQTXXIFXAG (SEQ ID NO:15) where "X" at any position can independently be any amino acid or unnatural amino acid. In one embodiment, the peptide of 11-30 amino acid residues comprising the sequence TXQTXXIFXAG (SEQ ID NO:15) does not include any of SEQ ID NO:11, SEQ ID NO:12, SEQ ID NO:13 and SEQ ID NO:14. The invention also provides a peptide of 15-30 amino acid residues comprising the sequence: TXQTXXIFXAGVXTA (SEQ ID NO:16) where "X" at any position can independently be any amino acid or unnatural amino acid. In one embodiment, the peptide of 15-30 amino acid residues comprising the sequence TXQTXXIFXAGVXTA (SEQ ID NO:16) does not include any of SEQ ID NO:11, SEQ ID NO:12, SEQ ID NO:13 and SEQ ID NO:14. The invention also provides a peptide of 11-30 amino acid residues comprising the sequence Y1XY2Y3XXY4Y5XY6Y7 (SEQ ID NO:17), where Y1 is threonine or a conserved amino acid, or unnatural amino acid, Y2 is glutamine or a conserved residue or unnatural amino acid, where Y3 is threonine or a conserved amino acid, or unnatural amino acid, where Y4 is isoleucine or a conserved amino acid, or unnatural amino acid, where Y5 is phenylalanine or a conserved amino acid, or unnatural amino acid, where Y6 is alanine or a conserved amino acid, or unnatural amino acid, where Y7 is glycine or a conserved amino acid, or unnatural amino acid, where X at any position can independently be any amino acid, or natural or unnatural chemically modified amino acid. Preferably at least one X or one Y in each sequence is an unnatural amino acid or a non-naturally occurring chemically modified amino acid. By, e.g., 11-30 amino acids, it is meant any number of amino acids between 11-30, i.e., 11, 12, 13, 14, . . . 29, or 30 amino acid residues. In one embodiment, the peptide consists of the sequence TXQTXXIFXAG (SEQ ID NO:15) or the sequence TXQTXXIFXAGVXTA (SEQ ID NO:16). In different embodiments, the interacting residues could be also mutated to conserved or similar residues that will maintain the interaction with BAX. In different embodiments, the peptides can be labeled with a label such as a fluorescent label or a radioactive label. In one embodiment, the peptides claimed herein are chemically synthesized peptides or peptides produced by recombinant DNA or cDNA. For example, the peptides can be made by liquid phase synthesis or by solid phase synthesis. The peptides can be synthesized, e.g., using recombinant DNA or cDNA. In one embodiment, the peptides are not directly obtained from a larger naturally-occurring BAX protein, for example, by digestion of the protein. In one embodiment, the peptides are isolated and purified peptides.

Methods are provided for inhibiting BAX comprising contacting BAX with the any of the peptides disclosed herein. The BAX can be in a living cell where preferably inhibition of BAX inhibits cell death. The BAX can in a subject, such as a mammal such as a human, and the agent is administered to the subject. The subject can have a disease or disorder associated with premature or unwanted cell death and characterized by abnormal activation, expression or function of BAX.

Diseases and disorder associated with premature or unwanted cell death and characterized with abnormal activation, expression or function of BAX include, for example, cardiovascular diseases and disorders (e.g. arteriosclerosis, heart failure, heart transplantation, aneurism, chronic pulmonary disease, ischemic heart disease, hypertension, thrombosis, cardiomyopathies), neurodegenerative and neurological diseases and disorders (e.g. Alzheimer's disease, Parkinson's disease, Huntington's disease, retinitis pigmentosa, spinal muscular atrophy, various forms of cerebellar degeneration, amyotrophic lateral sclerosis), liver diseases and disorders, kidney diseases and disorders, immunological disorders (e.g. organ transplant rejection, arthritis, lupus, IBD, Crohn's disease, asthma, multiple sclerosis, diabetes), ischemia (e.g. stroke, myocardial infarction and reperfusion injury), infertility (e.g. premature menopause, ovarian failure or follicular atresia), blood disorders (e.g. fanconi anemia, aplastic anemia, thalassemia, congenital neutropenia, myelodysplasia), renal hypoxia, hepatitis, asthma and AIDS. Diseases associated with inhibition of cell death and characterized by abnormal inhibition, expression or function of BAX include, for example, cancer and autoimmune diseases.

Method are also provided for identifying an agent as a candidate agent for inhibiting cell death comprising:

contacting BCL-2-associated X-protein (BAX) with one or more of any of the peptides disclosed herein in the presence of the agent and in the absence of the agent, and measuring binding of the one or more peptides to BAX, wherein decreased binding of the one or more peptides to BAX in the presence of the agent compared to binding of the one or more peptides to BAX in the absence of the agent indicates that the agent is a candidate agent for inhibiting cell death. In one embodiment, the peptides are fluorescently labeled, for example with fluorescein isothiocyanate (FITC).

As used herein, "BAX" is BCL-2-associated X-protein. In an embodiment, the BAX is mammalian. In a preferred embodiment, the BAX is a human BAX. In an embodiment, the BAX comprises consecutive amino acid residues having the following sequence:

```
                                          (SEQ ID NO: 1)
MDGSGEQPRGGGPTSSEQIMKTGALLLQGFIQDRAGRMGGEAPELALDPV

PQDASTKKLSECLKRIGDELDSNMELQRMIAAVDTDSPREVFERVAADME

SDGNENWGRVVALFYFASKLVLKALCTKVPELIRTIMGWTLDFLRERLLG

WIQDQGGWDGLLSYEGTPTWQTVTIEVAGVLTASLTIWKKMG.
```

In an embodiment of the methods described herein, the methods are useful for identifying therapeutic cell death inhibitors. In an embodiment of the methods described herein, the methods are useful for identifying therapeutic cell death activators.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods
Reagents—
Hydrocarbon-stapled peptide corresponding to the BH3 domain of BIM, BIM SAHB$_{A2}$: N-acetylated$^{145}$EIWIAQELRS5IGDS5FNAYYA$^{164}$-CONH$_2$ (SEQ ID NO:2), where S5 represents the non-natural amino acid inserted for olefin metathesis, was synthesized, purified and characterized as previously described by CPC Scientific (11).

Production of Recombinant BAX—
Human BAX wild type and mutants were generated using a standard PCR-based cloning strategy and PCR-based site-directed mutagenesis in pTYB1 vector (New England Biolabs) and constructs were confirmed by sequencing. Recombinant proteins are expressed in BL21 (DE3) codon+ E. coli strain and purified as previously described (16).

Size-Exclusion Chromatography—
Superdex 75 10/300 GL and 200 10/300 GL (GE Healthcare) columns were used for size exclusion chromatography of recombinant proteins and cell extracts. Recombinant protein was injected in columns equilibrated with a buffer containing 20 mM HEPES pH 7.2, 150 mM KCl, 1 mM DTT. 1 mg of cytosolic or membrane extracts was applied to a Superdex 200 10/300 GL equilibrated in buffer containing 10 mM Tris, pH 7.5, 1 mM EGTA, 200 mM Sucrose and Complete Protease Inhibitors. Fractions of 500 µl were collected, and 30 µl of each fraction was analyzed by SDS-PAGE and immunoblotting. All operations were run at 4° C. Gel filtration molecular weight markers (GE Healthcare) were also subjected to the columns to obtain a standard curve for the estimation of the molecular weight of the proteins.

Dynamic Light-Scattering—
The dynamic light scattering of various samples was measured using a DynaPro801 instrument from Wyatt Technology and *DYNAMICS* v.5.25.44 software for data collection and analysis. The protein samples after elution from the size-exclusion chromatography were centrifuged for 10 min at 13,000 rpm and loaded to plastic cuvettes. Typically, one hundred scans of five seconds was acquired for each 100 µl sample. Normalized intensity versus hydrodynamic radius (nm) measured in 20 mM HEPES pH 7.2, 150 mM KCl, 1 mM DTT buffer.

Crystallization—
Homogeneous BAX protein in 20 mM HEPES pH 7.2, 150 mM KCl, 1 mM DTT buffer was concentrated to 10 mg/ml using a filtration unit (Milipore). Initial screening of crystallization conditions for BAX wild type and mutants were carried out by the sitting-drop vapor-diffusion method using 96-well Intelli-Plates (Hampton Research) at 293 K. The BAX protein was concentrated to 10 mg/ml in 20 mM HEPES pH 7.2, 150 mM KCl, 1 mM DTT and centrifuged prior to crystallization setup. Diffraction quality rod-shaped crystals were generated in 0.1 M Bis-Tris pH 6.5, 1.5 M ammonium sulfate via the hanging-drop vapour-diffusion method using 24-well VDX plates (Hampton Research). 1 µl of protein solution and reservoir solution were mixed and equilibrated against 1 ml of reservoir solution. Crystals were cryoprotected by soaking for 5 s in 20 µl of cryoprotectant solution containing 0.1 M Bis-Tris pH 6.5, 1.5 M ammonium sulphate and 25% (v/v) glycerol, and flash-frozen in liquid nitrogen.

Data Collection and Structure Determination—
X-ray diffraction data were collected at beamlines in National Synchrotron Light Source and Advanced Photon Source. All data were integrated and scaled with HKL2000 (19) and further processing was carried out with CCP4 software suite (20). The crystal structure of BAX was determined by molecular replacement method using the monomeric NMR structure of BAX (PDB ID: 1F16) as a search model. Model was mutated to poly Ala. Multiple cycles of manual editing and adjustment of the model using COOT (21) followed refinement by simulated annealing, energy minimizations and individual isotropic B factor refinement with REFMAC (22). A break chain of the loop between helices α1 and α2 was realized due to poor diffraction data at the model building stage. The final models were validated with PROCHECK (23), PISA (24) and molecular models were rendered using PYMOL (25). Data collection and statistics are summarized in Table 2.

NMR Samples and Spectroscopy—
Protein samples were prepared in 25 mM sodium phosphate, 50 mM NaCl solution at pH 6.0 in 5% D$_2$O. Correlation $^1$H-$^{15}$N HSQC, $^1$H-$^{15}$N TROSY spectra and triple resonance spectra for backbone $^1$H, $^{13}$C, $^{15}$N assignments of BAX P168G monomer: HNCO, HNCA, HNCOCA, HNCACB, HNCOCACB and N$^{15}$NNH-NOESY were acquired at 25° C. on a Inova 600 MHz NMR spectrometer equipped with a cryogenic probe, processed using Topsin, and analyzed with CCPNMR (26). BAX wild type cross-peak assignments were applied as previously reported (11, 16). The weighted average chemical shift difference Δ at the indicated molar ratio was calculated as $\approx((\Delta\delta H^1)^2+(\Delta\delta N^{15}/5)^2)$ in p.p.m. The absence of a bar indicates no chemical shift difference, or the presence of a proline or a residue that is overlapped and not used in the analysis. The significance threshold for backbone amide chemical shift changes was calculated based on the average chemical shift across all residues plus the standard deviation, in accordance with standard methods.

BAX Dimerization Assays—

BAX wild type and mutants were concentrated to ~0.5 mM in BAX buffer (10 mM HEPES pH 7, 150 mM KCl, 1 mM DTT) and incubated at 20° C. for 1-3 days before diluting to a total volume of 250 µl and loaded onto a Superdex 75 HR 10/30 size exclusion column (GE Healthcare). These conditions allow a controlled dimerization process than aggregation due to BAX activation. Separation of monomeric and dimeric BAX was achieved using a flow rate of 0.5 ml/min at 4° C. The chromatogram traces show the monomeric and dimeric peaks at ~11.8 and ~10.4 ml, respectively. Protein standards (GE Healthcare) were used to calibrate the molecular mass of gel filtration peaks. Chromatogram traces are representative of several independent preparations of freshly SEC-purified monomeric BAX.

BAX Crosslinking—

Dimerization was detected using a crosslinking approach by incubating BAX at indicated doses with 20×BMH on ice for 15 min followed by quenching with 1 mM DTT. Samples were denatured at 90 degrees and analyzed with SDS-PAGE.

Liposomal Permeabilization Assay—

Liposomes were composed of the following molar percentages of lipids (Avanti Polar Lipids): phosphatidylcholine, 48%; phosphatidylethanolamine, 28%; phosphatidylinositol, 10%; dioleoyl phosphatidylserine, 10%; and tetraoleoyl cardiolipin, 4% and were loaded with ANTS/DPX (Molecular Probe) upon extrusion. BAX (400 nM) was combined with BIM SAHB$_{A2}$ at the indicated concentrations in 96-well format (Corning) and then liposomes were added (10 µl from 50 mM total lipid stock) in assay buffer (10 mM HEPES, pH 7, 200 mM KCl, 5 mM MgCl$_2$, and 0.2 mM EDTA) to a final volume of 100 µl. ANTS/DPX release was quantified based on the increase in fluorescence intensity that occurs when the ANTS fluorophore is separated from the DPX quencher upon release from the liposomes into the supernatant. Fluorescence ($\lambda_{ex}$=355 nm and $\lambda_{em}$=520 nm) was measured over time at 30° C. using a Tecan Infinite M1000 plate reader. The percentage release of ANTS/DPX at 90 min was calculated as percentage release=$((F-F_0)/(F_{100}-F_0))\times100$, where $F_0$ and $F_{100}$ are baseline and maximal fluorescence, respectively. 1% Triton treatment is used to determine the maximum amount of liposomal release per assay, and this value sets the 100% value.

Cell Culture, Cell Transfection and Apoptosis Assay—

Wild type MEFs and SV40-transformed Bax$^{-/-}$ Bak$^{-/-}$ (DKO) MEFs were maintained in DMEM high glucose (Invitrogen) supplemented with 10% FBS, 100 U ml$^{-1}$ penicillin/streptomycin, 2 mM 1-glutamine, 0.1 mM MEM nonessential amino acids, and 50 µM β-mercaptoethanol. Reconstitution of BAX and BAX mutant into DKO cells was achieved by retroviral transduction of BAX-IRES-GFP or BAX(P168G)-IRES-GFP plasmids, followed by MoFlo sorting for GFP-positive cells. The production of retroviruses was performed as described previously (17). Comparable expression of BAX WT and mutant protein was confirmed by western analysis. For staurosporine treatment, MEFs (5×10$^4$ per well) were seeded in six-well clear-bottom plates for 16-18 hours in serum-containing media and then treated with 1 µM staurosporine. For transient retroviral transduction of BAX or BAX mutant, DKO MEFs were infected with retrovirus expressing BAX or BAX mutant for 30-36 hours. Cell death was quantified by annexin-V (BioVision) staining. Flow cytometry was performed using a LSRFortessa (BD Biosciences) and data were analyzed using FACSDiva (BD Biosciences). The expression of BAX or BAX mutant was assessed by anti-BAX western blot. P values for statistical analyses were obtained using Student's t test.

Subcellular Fractionation—

MEFs were maintained in DMEM (Invitrogen) supplemented with 10% FBS, 100 U ml$^{-1}$ penicillin/streptomycin, 2 mM 1-glutamine, 0.1 mM MEM nonessential amino acids, and 50 µM β-mercaptoethanol. MEFs (20×10$^6$ per well) were seeded in a 150 mm dish for 12 hours. To isolate cytosol and mitochondrial fractions, cells were lysed by Dounce homogenizer in lysis buffer LB containing 10 mM Tris, pH 7.5, 1 mM EGTA, 200 mM Sucrose and Complete Protease Inhibitors. The cell lysates were centrifuged at 700×g for 10 min to remove unlysed cells and nuclei. The supernatants were centrifuged at 12000×g for 10 min at 4° C. and the resulting pellet was collected as the mitochondrial fraction. The membrane pellet was resuspended in LB+1% CHAPS.

Western Blotting—

20 µg of whole-cell protein was electrophoretically separated on 4-12% NuPage (Invitrogen) gels, transferred to Immobilon-FL PVDF membranes (Millipore) and subjected to immunoblotting. For visualization of proteins with Odyssey Infrared Imaging System (LI-COR Biosciences) membranes were blocked in PBS containing 2.5% milk powder. Primary BAX antibody (Cell Signaling 2772S) was incubated overnight at 4° C. in a 1:1,000 dilution. After washing, membranes were incubated with an IRdye800-conjugated goat anti-rabbit IgG secondary antibody (LI-COR Biosciences) in a 1:5,000 dilution. Proteins were detected with Odyssey Infrared Imaging System.

BAX Conformational Change Assay—

Cytosolic fractions were subjected to immunoprecipitation followed by immunoblotting against total BAX. Briefly, 100-300 µg total protein was collected and incubated with pre-equilibrated protein G Sepharose beads (Santa Cruz Biotechnology Inc.) for 1 hour. The precleared samples were then incubated with the 6A7 antibody (6 µg/ml) (1:1,000, sc-23959, Santa Cruz Biotechnology) for four hours at 4° C. followed by the addition of pre-equilibrated protein G Sepharose beads for 1 hour. The beads were pelleted, washed with lysis buffer 3 times at 4° C., and protein eluted by heating the beads at 90° C. for 10 minutes in LDS/DTT loading buffer. The immunoprecipitates were subjected to electrophoresis and Western blot analysis using anti-BAX antibody (1:1,000) (Cell Signaling 2772S).

Results

The current invention makes use of the discovery that cytosolic BAX forms a dimeric autoinhibited form that is mediated by the N-terminal trigger site of one protomer and a novel interacting C-terminal surface that includes α9 of the second protomer. These interacting protein surfaces of BAX provide important insights for understanding the structural basis of BAX inhibition and designing drugs for pharmacological modulation of BAX. It was found that monomeric wild type BAX (BAX WT), in the absence of a BH3 activating domain, reversibly forms a dimer over time as measured by size exclusion chromatography (SEC) and polyacrylamide gel electrophoresis (PAGE). A single point mutation such as P168G in the α8-α9 loop of BAX, which controls helix α9 mobilization, generates the identical dimeric peak by SEC. BAX P168G forms a more stable dimer, which persists several days at room temperature.

Figure 1A:
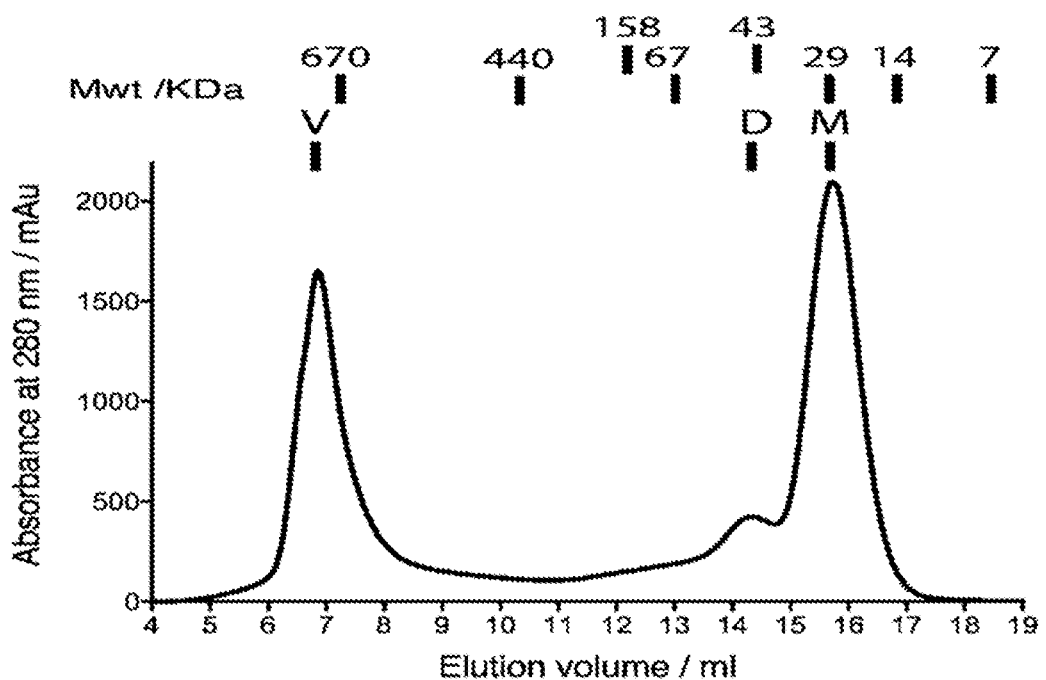
FIG. 1A-1D. BAX forms an inactive dimer conformation. (A) Representative size exclusion chromatography (SEC) trace of recombinant BAX analyzed by Superdex 200 (HR 10/30) gel filtration column showing eluted monomer (M) and dimer (D) peaks at ~15.8 ml and ~14.2 ml, respectively. (B) Recombinant BAX (rec. BAX), cytosolic extract of WT MEF and DKO MEF, and cytosolic extract from WT MEF treated with 1% Triton X-100 (cyt. BAX+1% Triton) were analyzed by Superdex 200 (HR 10/30) gel filtration. Fractions corresponding to indicated molecular weights and elution volumes were analyzed by anti-BAX immunoblotting. (C) Dimerization of purified monomeric recombinant BAX at different doses was analyzed by Superdex 75 (HR 10/30) gel filtration chromatography showing eluted monomer (M) and dimer (D) peaks at ~11.8 ml and ~10.4 ml respectively. (D) Liposome release assay plotted in kinetic format of SEC-isolated BAX monomer and dimer without and with stapled peptide-based BAX activator BIM SAHB$_{A2}$ at indicated concentrations. Data shown in (A-C) representative of three experiments and in (D) are mean from four independent experiments.
Figure 1B:
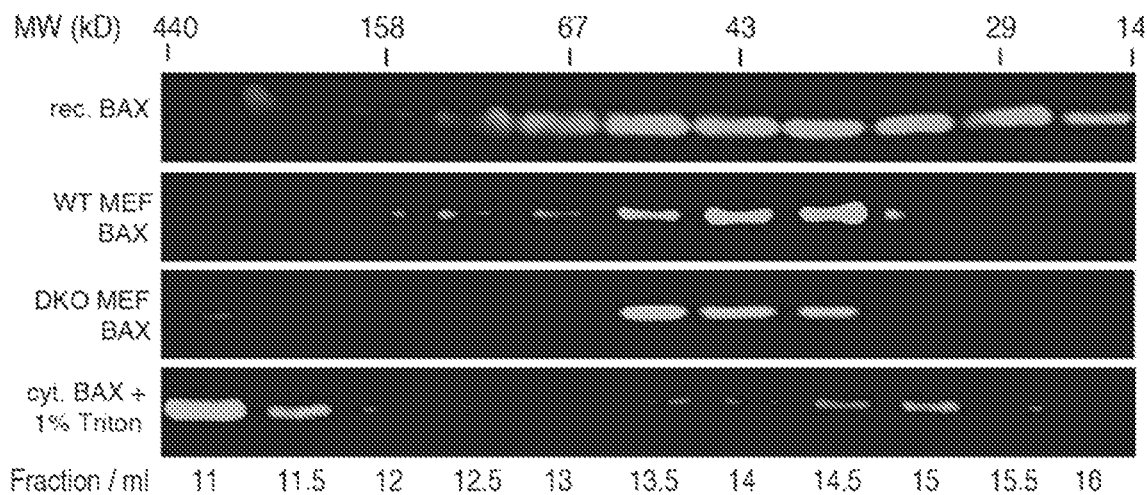
Figure 5:
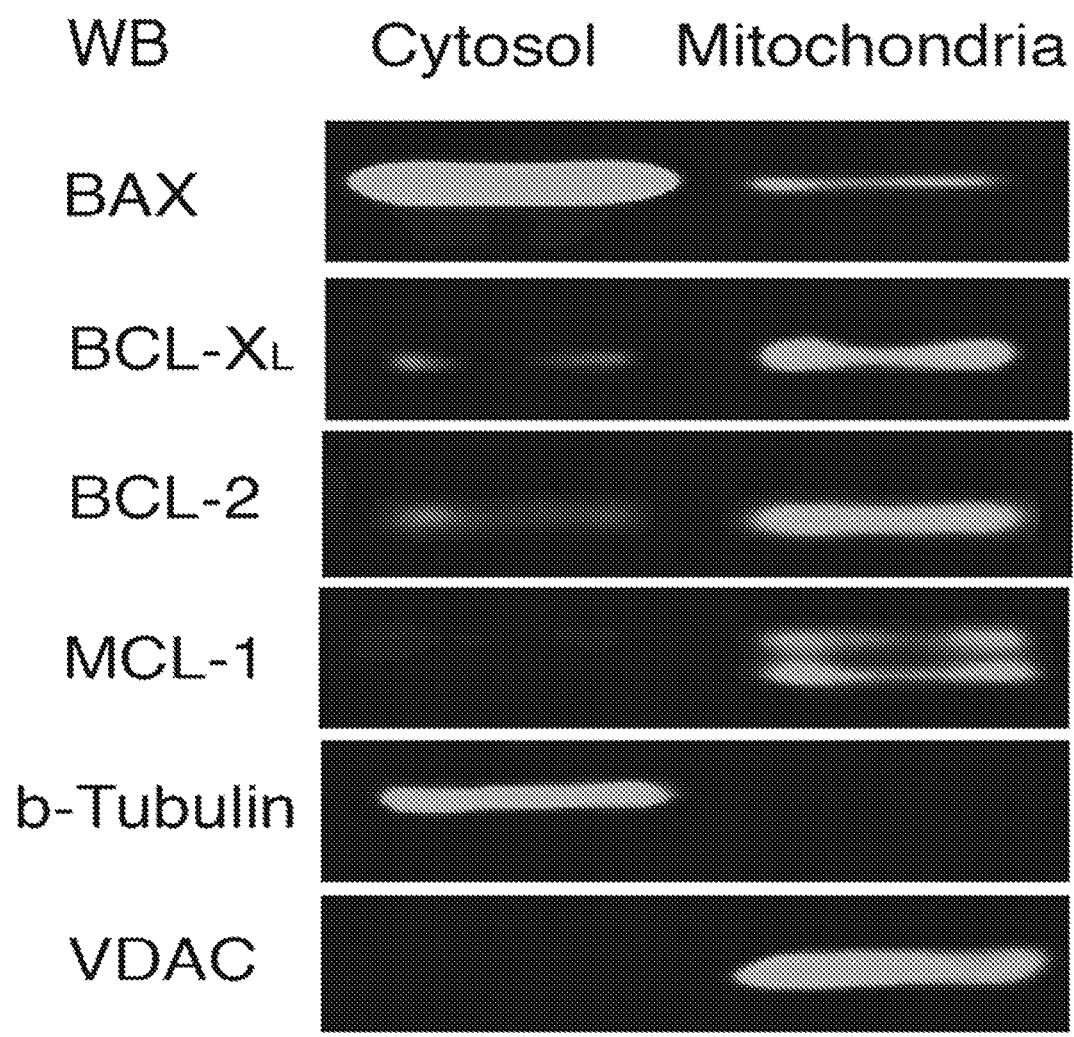
FIG. 5. Anti-apoptotic BCL-2, BCL-$X_L$ and MCL-1 proteins, established to interact with BAX, are in very low levels in the cytosol compared to BAX and predominantly reside at the mitochondria. Protein levels of BAX, BCL-2, BCL-$X_L$ and MCL-1 in cytosolic and mitochondrial fractions of MEFs as determined by immunodetection. Separation of the cytosolic from the mitochondrial fraction of MEFs is confirmed with b-tubulin and VDAC antibodies respectively.
Figures 6A, 6B:
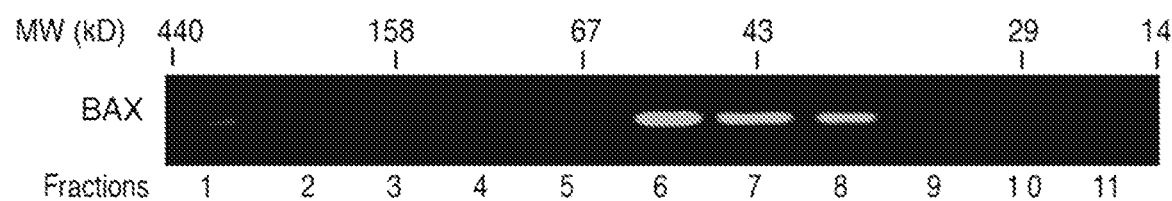
FIG. 6A-6B. Cytosolic BAX in dimer conformation is inactive as determined by immunoprecipitation assay with the 6A7 antibody that specifically recognizes the active conformation of BAX. (A) Size-exclusion chromatography analysis of cytosolic extracts of MEFs using Superdex 200 10/300 GL gel filtration column, indicating the elution profile of BAX WT in dimer size (B) Fractions 6 and 8 of BAX WT are 6A7 negative and failed to co-immunoprecipitate with the 6A7 antibody. As a positive control, fractions were incubated with 1% Octylglucoside detergent that activates BAX and exposes the 6A7 epitope on BAX.

The conformations of recombinant BAX and cytosolic BAX from mouse embryonic fibroblasts (MEFs) were investigated. Recombinant full-length BAX was purified from *E. coli* extracts using chitin affinity chromatography followed by size-exclusion chromatography (SEC) (17). Recombinant BAX elutes from SEC predominantly in a peak that corresponds to its monomeric form (11,17) and additionally in a second distinct peak that corresponds to a dimeric form (FIG. 1A, 1B). Cultured MEFs were lysed, without detergents in the buffer, and cytosolic and mitochondrial fractions were separated followed by fractionation with SEC. Surprisingly, endogenous BAX eluted in fractions that corresponds to a BAX dimer using the same SEC conditions for recombinant BAX (FIG. 1B). Next, SEC was repeated with MEFs that are doubly deficient in $BAX^{-/-}$ and $BAK^{-/-}$ (DKO MEFs) and stably express human BAX at endogenous levels, and again cytosolic BAX appeared to be a dimer (FIG. 1B). To exclude the possibility that cytosolic BAX is a heterodimer with anti-apoptotic BCL-2 proteins in the cytosol, cytosolic and mitochondrial fractions were subjected to western blot analysis, confirming that anti-apoptotic proteins are in very low levels in the cytosol compared to BAX and predominantly reside at the mitochondria (FIG. 5). Furthermore, the cytosolic BAX dimer is in inactive conformation as proved by immunoprecipitation analysis using the 6A7 antibody that only recognizes the active BAX conformation (FIG. 6) (18). However, when cytosolic BAX was treated with a detergent that promotes its activation, BAX appeared predominantly at high molecular weight, presumably forming the BAX oligomer. In addition, a minor portion eluted as BAX monomer, suggesting that BAX activation requires disruption of the BAX dimer conformation (FIG. 1B). Taken together, these results demonstrate that cytosolic BAX predominantly adopts a dimeric and inactive conformation.

Figure 1C:
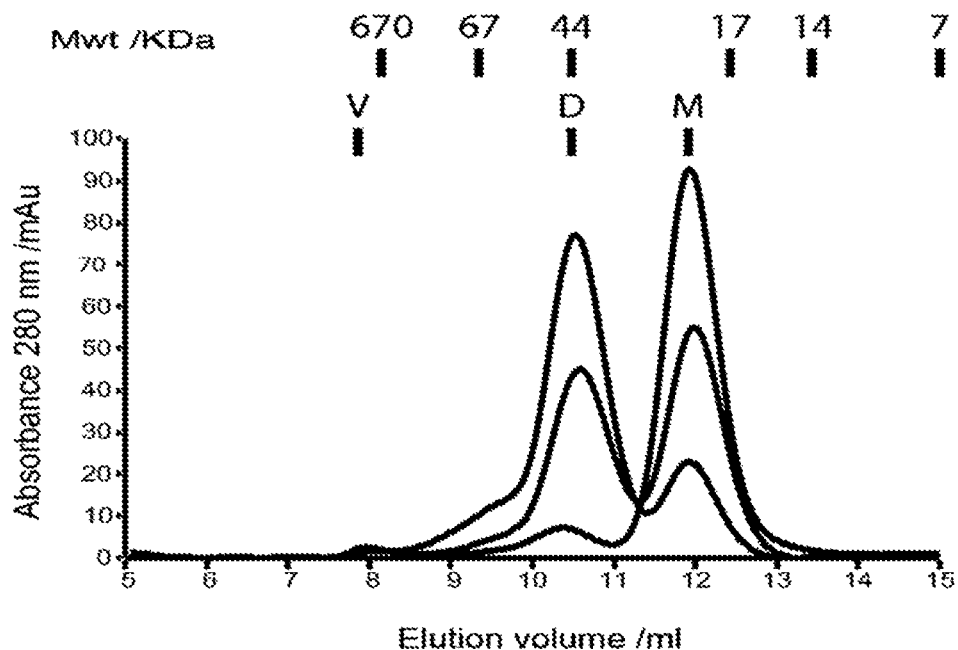
Figure 1D:
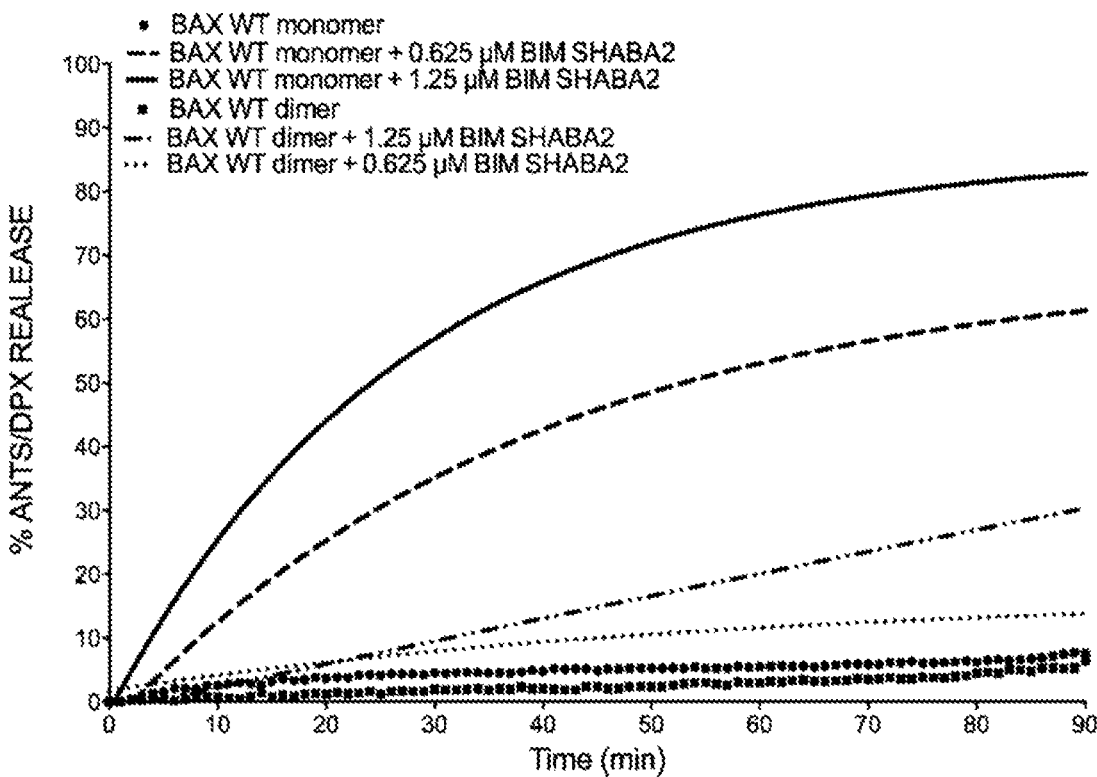
Figure 7:
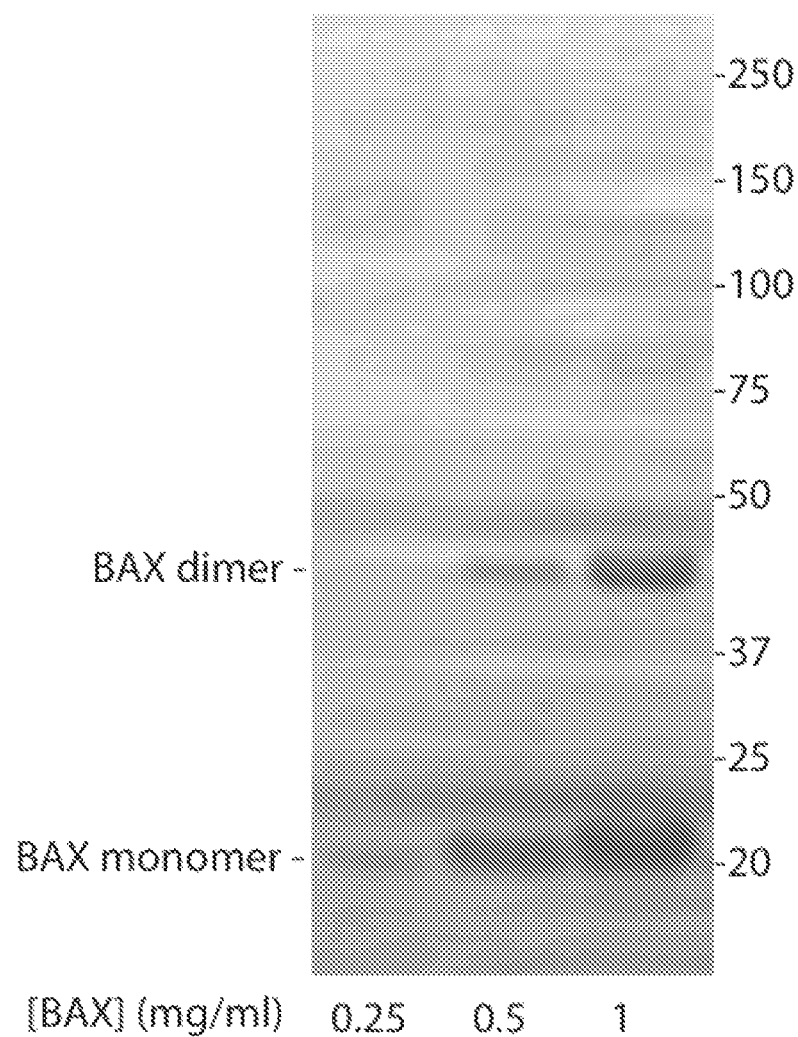
FIG. 7. BAX dimerization is detected using a crosslinking approach. Coomassie stains of BAX in polyacrylamide gel electrophoresis (SDS-PAGE) after treatment with 20× BMH crosslinking reagent for 15 min at indicated BAX concentrations.

To elucidate the physiological role of the cytosolic BAX dimer conformation, the molecular basis of BAX dimerization was investigated. First, a method to reproducibly generate sufficient amounts of the BAX dimer was established by incubation of the BAX monomer at high concentrations as shown by SEC or treatment with the BMH crosslinker followed by polyacrylamide gel electrophoresis (FIGS. 1C, 7). The monomeric and dimeric peaks of SEC were confirmed by dynamic light scattering to correspond to homogenous populations of BAX monomer (~21KD) and dimer (~42KD) respectively (Table 1). In liposomal assay, while the BAX monomer is not able to permeabilize membranes alone, it was activated and induced membrane permeabilization upon activation by the hydrocarbon-stapled BIM BH3 helix, BIM $SAHB_{A2}$, (FIG. 1D) (11,12). In contrast, SEC-isolated BAX dimer alone showed no capacity to induce membrane permeabilization in liposomal permeabilization assays and upon addition of BIM $SAHB_{A2}$ it was nearly inactive (FIG. 1D). Therefore, the BAX dimer conformation is inactive and resistant to activation compared to monomeric BAX suggesting that the BAX dimer may form an autoinhibited conformation.

Figure 2A:
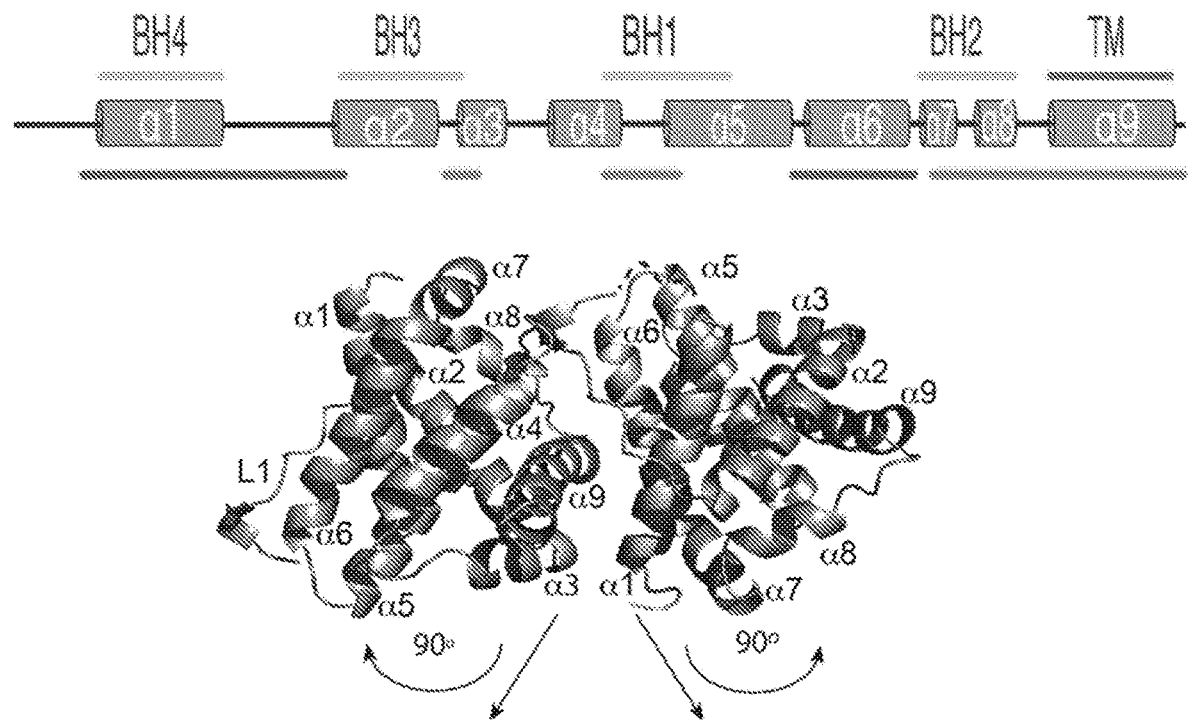
FIG. 2A-2B. Crystal structure of the inactive BAX dimer. (A) Ribbon representation of the BAX dimer crystal structure. Dimerization interaction interfaces are shown for each BAX protomer. Helices (a) and loops (L) are depicted on the structures. Secondary structure representation cartoon showing the location of the BCL-2 homology domains (BH), the transmembrane region (TM), and the dimerization interaction interfaces. (B) Ribbon representation of each BAX protomer in view related to the representation in (A) at 90 degrees rotation around a vertical axis, showing the N-terminal and C-terminal dimerization interfaces.
Figure 2B:
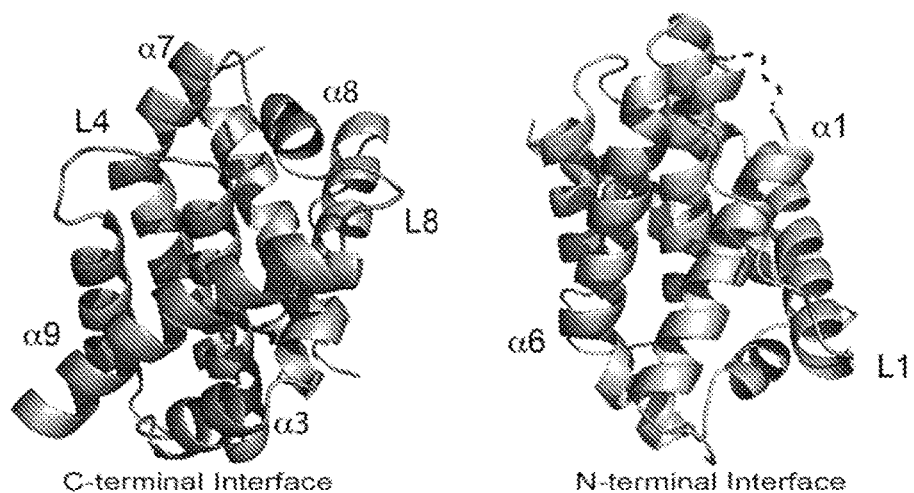
Figure 3A:
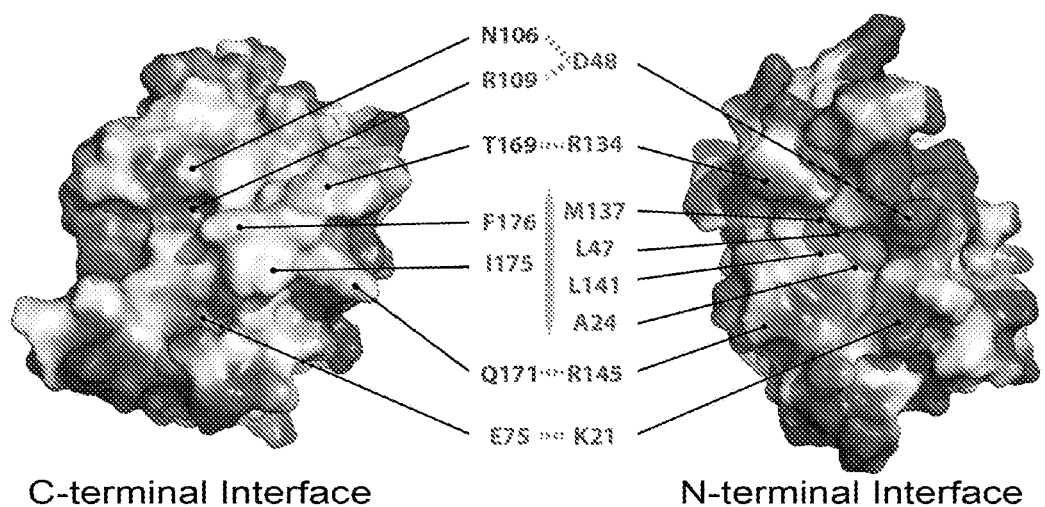
FIG. 3A-3E. Structural details of the BAX dimerization mechanism. (A) Calculated vacuum electrostatics of the C-terminal and N-terminal interaction surfaces of each BAX protomer in the dimer showing the position of complementary hydrophobic, polar and charged residues. (B) Cartoon representation of the BAX dimer showing the protomers labelled by their dimer interaction interface. The interacting residues are shown in sticks and are highlighted in three different regions of the dimer interaction interface: (C) hydrophobic core of the dimerization interface involving α9 residues I175 and F176 of one protomer and residues M20 and A24 from α1, M137 and L141 from α6 and L47 and V50 from α1-α2 loop, (D) hydrogen bonds between the following residue pairs of different BAX protomer: R145 of α6 and Q171 of α9, E17 of α1 and M74 and E75 of α3 and salt bridge between K21 of α1 and E75 of α3 residue pair and (E) hydrogen bonds between the following residue pairs of different BAX protomer: A46 of α1-α2 loop and Y164 of α8, E44 of α1-α2 loop and W107 of α5, D48 of α1-α2 loop and N106 of α5 and salt bridge between D48 of α1-α2 loop and R109 of α4-α5 loop residue pair.
Figure 3B:
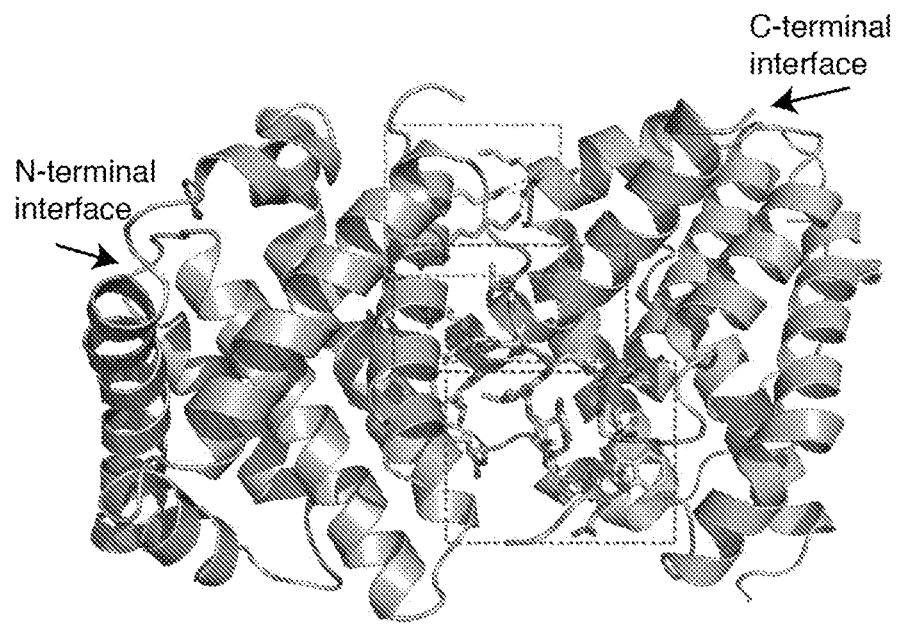
Figure 3C:
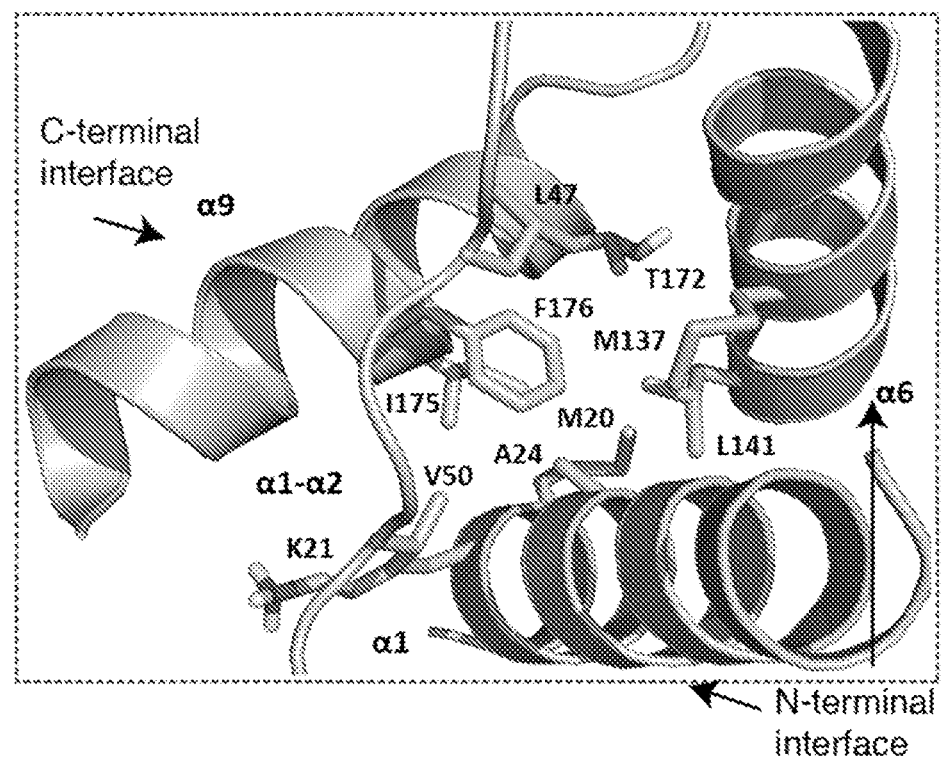
Figure 3D:
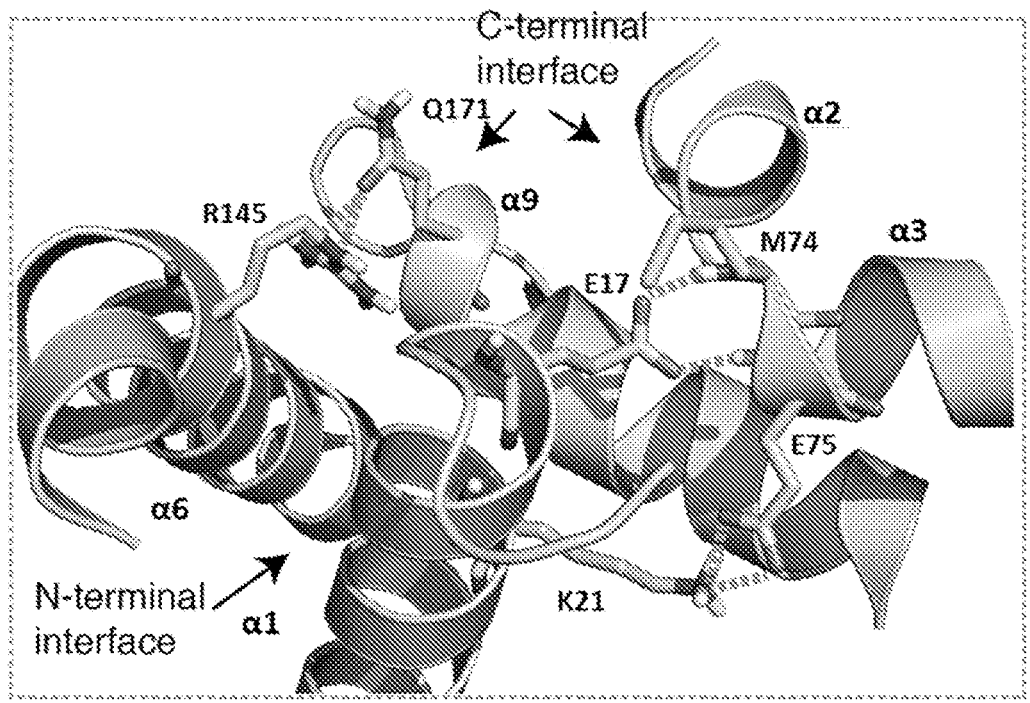
Figure 3E:
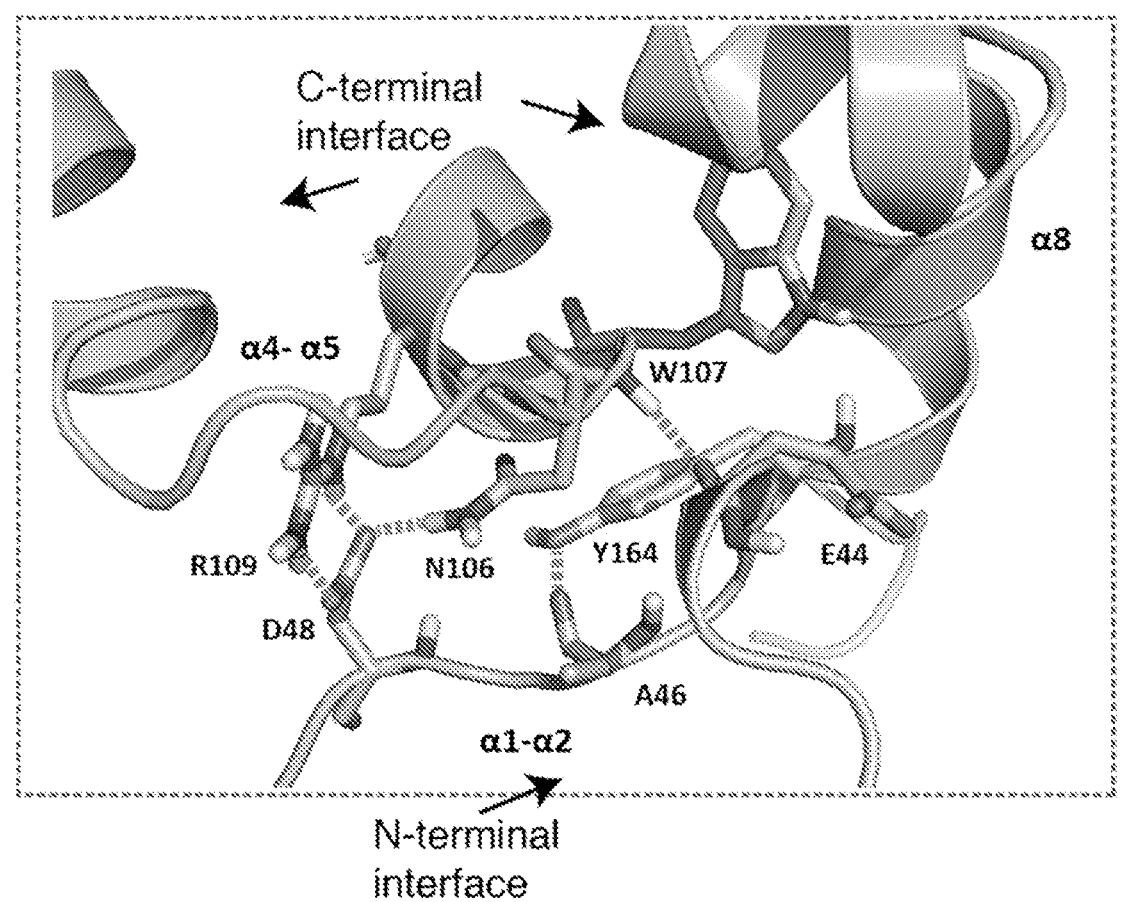
Figure 8:
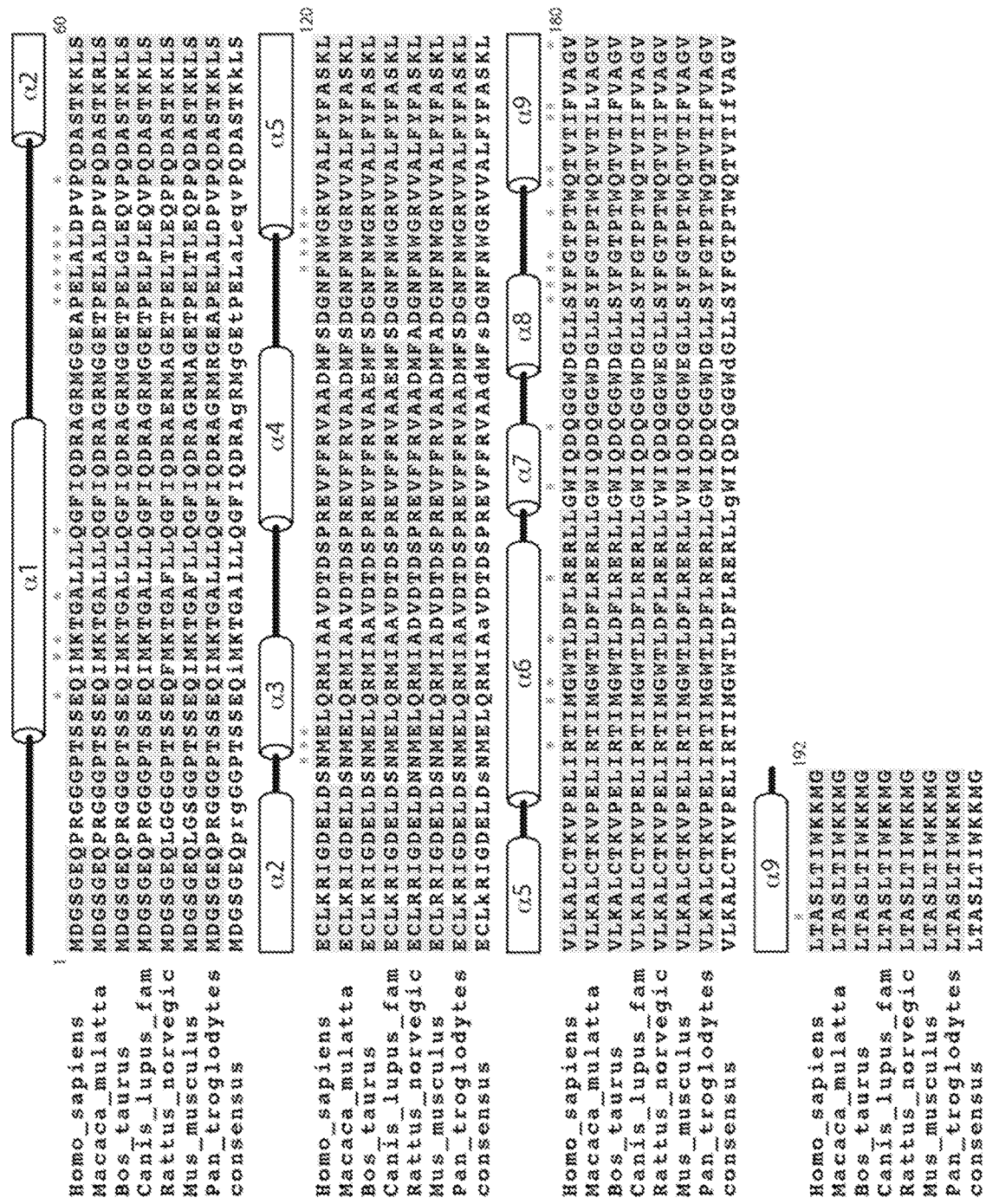
FIG. 8. Protein sequence alignment of BAX sequences from indicated species. Protein sequence alignment of BAX sequences showing identical residues shaded in light grey; conserved residues, similar residues and different residues shaded in white. Asterisks denote the positions of residues in each BAX protomer that is involved in interactions at the interface of the BAX dimer structure. Secondary structure symbols of helices and loops are based on the crystal structure of BAX dimer. From top to bottom of sequences: SEQ ID NO:3 (*Homo sapiens*) to SEQ ID NO:10 (consensus).
Figure 9A:
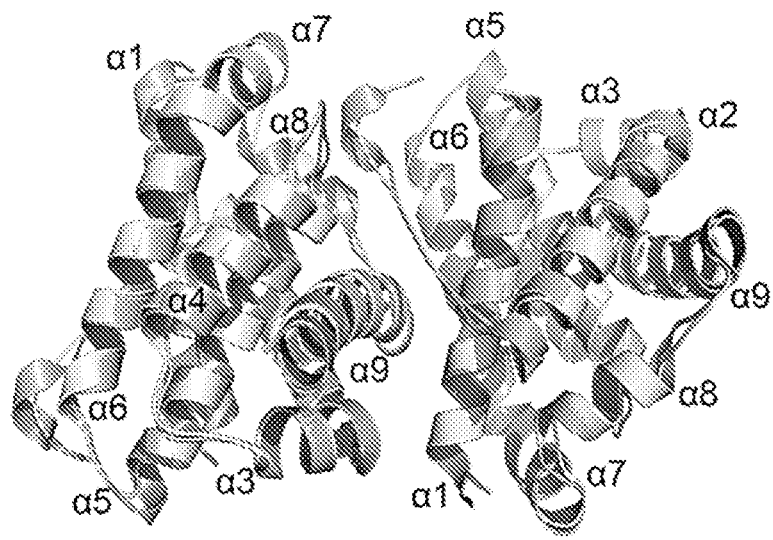
FIG. 9A-9C. Crystal structure of mutant BAX G67R dimer indicates the same dimerization mechanism of BAX as determined in the structure of the BAX P168G dimer. (A) Structural alignment of the crystal structure of BAX G67R dimer (light grey) and BAX P168G dimer (darker grey). (B) Structural alignment of BAX G67R protomer (light grey) and BAX P168G protomer (darker grey) crystal structures in view centered around helix α5. (C) Structural alignment of BAX G67R protomer (light grey) and BAX P168G protomer (darker grey) crystal structures in view centered around the N-terminal trigger site.
Figure 9B:
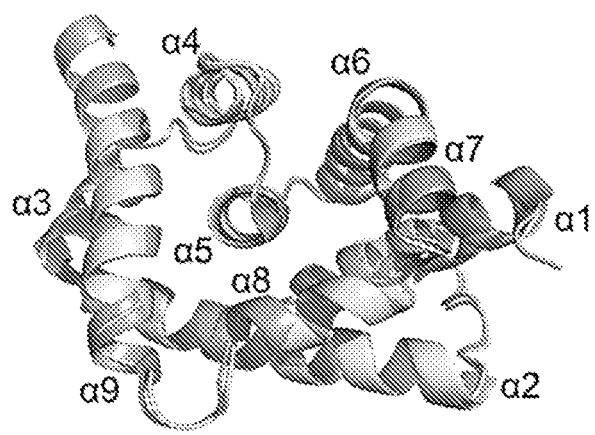
Figure 9C:
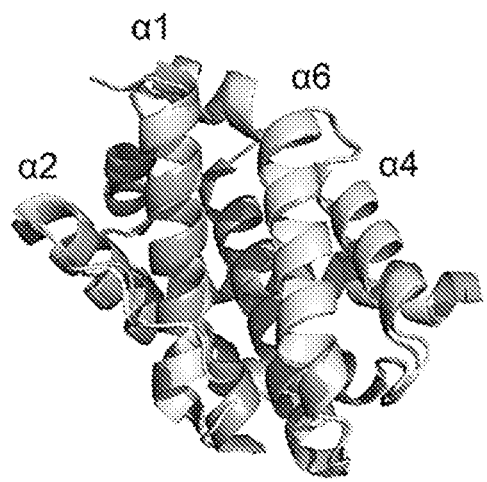

X-ray crystallographic studies were performed to gain further insights into the inactive BAX dimer. The stability of the SEC dimer peak was monitored with wild type BAX and mutants to predict successful crystallization. Quality of crystals for diffraction was better with mutants that produce more stable dimer than wild type BAX. The BAX P168G mutant, which does not alter the structure of BAX but reduces the dynamics of the α8-α9 loop, successfully produced crystals and a native X-ray data set was obtained to a resolution of 1.9 Å. The crystal structure was solved and refined by a molecular replacement approach using the NMR structure of full-length BAX as a search model (Table 2). The asymmetric unit contained two BAX molecules with excellent electron density map, in which all BAX residues could be traced except from residues of the N-terminal unstructured region (residues 1-13) and four residues of the unstructured loop between helices α1 and α2 (residues 37-40) (FIG. 2). The dimerization interface is formed by conserved residues and is extensive, burying almost 1900 Å$^2$ surface area (FIGS. 2A and 8). Remarkably, the BAX dimer structure reveals a dimerization interface that includes the interaction of two structural surfaces critical for the activation of BAX; the N-terminal trigger site from one BAX protomer and a novel C-terminal surface from the second BAX protomer that includes the C-terminal α9 helix (FIGS. 2B, 14). Of note, this dimeric structure and dimerization interface is irrelevant of the BAX P168G mutant as a BH3 residue mutant, G67R, that introduces a new hydrogen bond with helix 1, yields the same asymmetric dimer conformation as determined by X-ray crystallography at resolution of 3.3 Å (FIG. 9, Table 2).

The BAX protomers within the asymmetric BAX dimer structure resemble the inactive monomeric BAX structure determined by solution NMR, however, they have noticeable differences in orientation of helices and conformation of loops (backbone r.m.s.d. of 2.1A) (17). Most pronounced differences correspond to residues located in the N-terminal trigger site surface, including helices α1, α6, α2 and α1-α2 loop. Furthermore, the comparison with the structure of full length BAX bound to the BIM BH3 helix (backbone r.m.s.d. 3.0 Å) (11) indicates that, in the asymmetric dimer, the α1-α2 loop is in a closed conformation, forming specific intramolecular contacts with helices α1 and α6, whereas the BIM BH3-bound BAX structure has the α1-α2 loop in an open and active conformation (11,12). Therefore, the structural analysis indicates that the asymmetric dimer structure contains two BAX molecules in distinct but inactive conformation in agreement with the evidence of the cytosolic inactive BAX dimer (FIG. 1).

The asymmetric BAX dimer conformation highlights two novel interaction surfaces of BAX (FIG. 3). The interaction surface of one BAX protomer includes mostly the BAX trigger site residues previously identified for binding to BIM $SAHB_{A2}$ with a number of additional interactions at its periphery (11). Moreover, the interaction site at the C-terminal surface is a novel and unforeseen binding surface of BAX that includes the C-terminal helix α9. The C-terminal binding surface has a hydrophobic center from solvent exposed hydrophobic residues of α9 that are surrounded by polar and charged residues of helices α8, α7, α3, the α4-α5 loop and the α8-α9 loop (FIG. 3A). The N-terminal binding surface has a hydrophobic center from solvent exposed hydrophobic residues of α1, α6 and the α1-α2 loop that are surrounded by charged residues, which complement charged residue of the C-terminal binding surface (FIG. 3A). The core of the dimerization interface is hydrophobic (FIG. 3B,C). Several residues form a network of hydrophobic interactions that complement the binding of helix α9 to the N-terminal BH3-binding site (FIG. 3C). However, a number of hydrogen bonds and salt bridges contribute to the dimer formation and stability (FIG. 3B, D, E). Thus, hydrophobic, polar interactions and salt bridges are involved in the extensive and highly complementary dimerization interface.

Figure 10A:
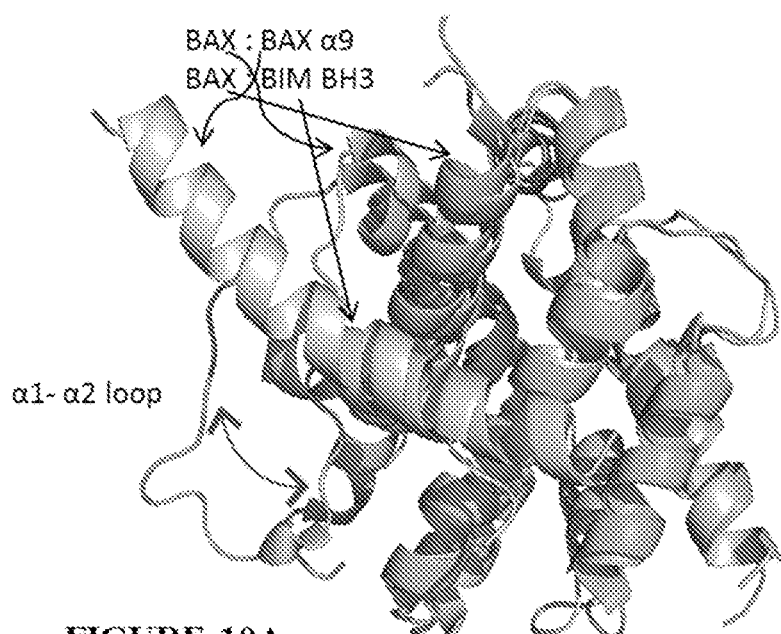
FIG. 10A-10C. Structural insights of cytosolic BAX regulation mechanisms. A) Structural alignment of the BAX protomer:α9 complex and BAX monomer:BIM BH3 complex in ribbon representation showing α9 helix and BIM BH3 helix bound orientations to the N-terminal trigger site. The α1-α2 loop in a closed conformation in the BAX protomer:α9 structure and open conformation in the BAX monomer:BIM BH3 structure. Cartoon representation of the B) BAX monomer:BIM BH3 interaction and C) BAX protomer:α9 interaction, highlighting key interacting residues in sticks. Color codes are indicated. Specifically, in the BIM BH3 bound structure (B) the hydrophobic surface of the BAX N-terminal trigger site, comprising residues A24, L25, L27 of α1 and L141, W139, G138, M137 of α6, forms extended hydrophobic interactions with conserved hydrophobic residues F159, I155, L152, and A149 of BIM BH3 (also FIG. 11B). Additional stabilizing interactions occur between Q28 and Q32 of BAX and N160 of BIM BH3 and complementary charge interactions between residues K21, R134 and E131 of BAX and E158E, D157 and R153 of BIM BH3 (FIG. 10B and FIG. 11B). In the dimer BAX structure (C), residues A24, L25, Q28 and Q32 from α1 interact instead with residues Q52, V50 and D48 of the α1-α2 loop of the same BAX molecule, generating an alternative hydrophobic cavity formed from the positioning of α1 and the α1-α2 loop, which facilitates the interaction with α9 residues I175 and F176 of the adjacent BAX molecule (also FIG. 11A). The closed α1-α2 loop conformation also positions polar and charged residues of the loop to make stabilizing intermolecular interactions (C). These structural insights provide strong evidence that cytosolic BAX forms an autoinhibited dimer which occludes key interactions required for its activation and mitochondrial translocation.
Figure 10B:
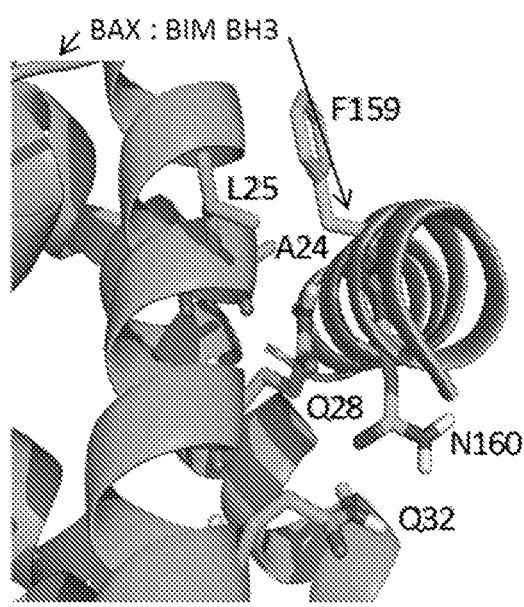
Figure 10C:
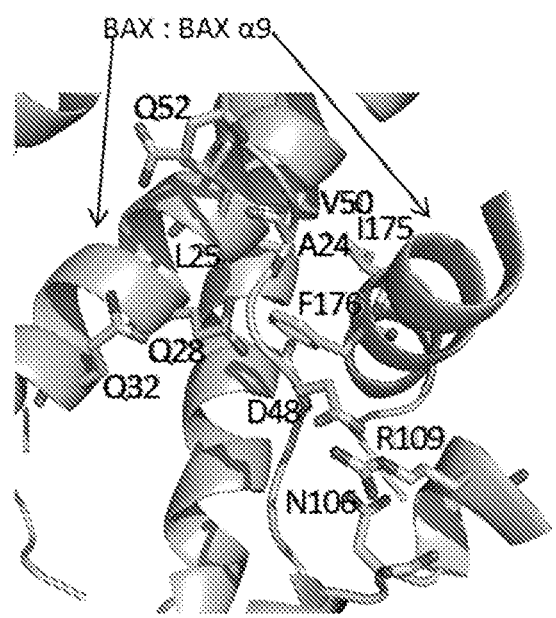
Figure 11A:
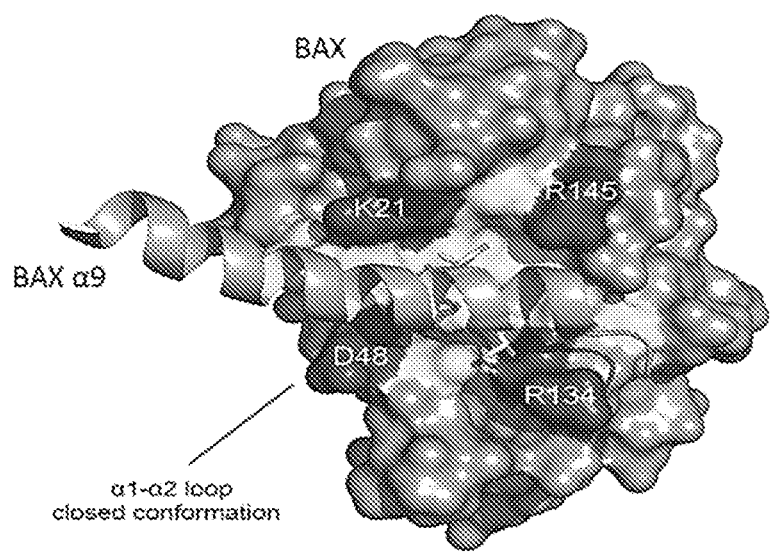
FIG. 11A-11B. Structural differences of the BAX's N-terminal binding site bound to α9 (taken from BAX P168G dimer structure) and BIM BH3 (PDB ID: 2KW7) peptides provide structural insights of cytosolic BAX regulation. N-terminal surfaces of BAX shown in grey and hydrophobic (lighter grey), positively charged (K21, R134, and R145) and negatively charged (D48 and E131) residues of the BAX trigger site and α1-α2 loop are highlighted. (A) BAX α9 binding with its hydrophobic residues make contacts with hydrophobic residues of the α1, α6 and α1-α2 loop, maintaining the structure of BAX in inactive conformation and α1-α2 loop in closed conformation. (B) BIM BH3 binding and its hydrophobic residues make contacts with hydrophobic residues of α1 and α6, ensuing a conformational change in α1-α2 loop to an open conformation and change in the orientation of α1 and α6 residues. Furthermore, BIM BH3 has favorable electrostatic interactions with the charged residues of α1 and α6 at the periphery of the hydrophobic site.
Figure 11B:
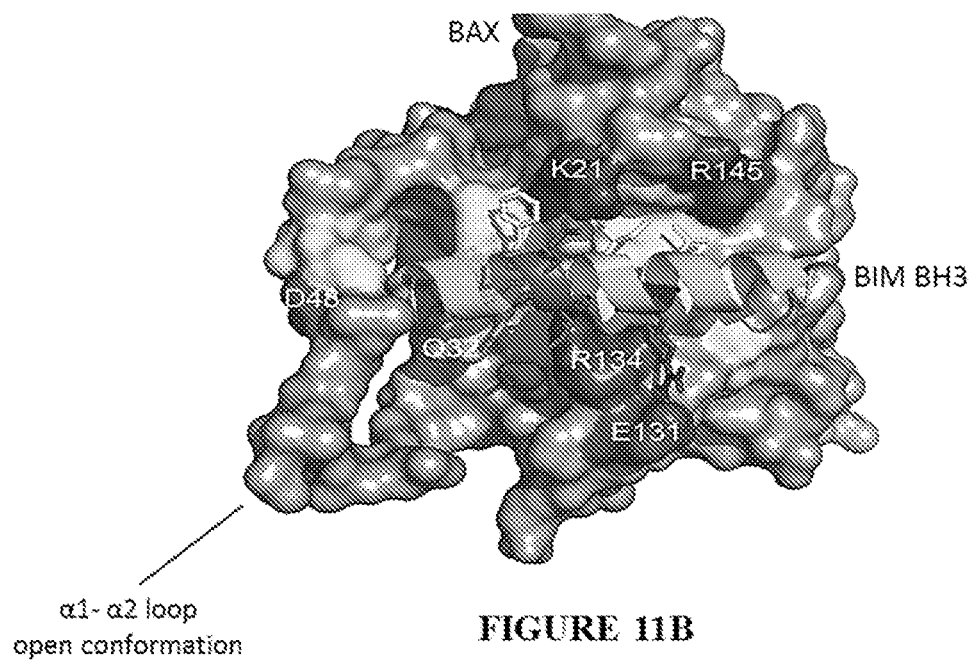
Figure 12:
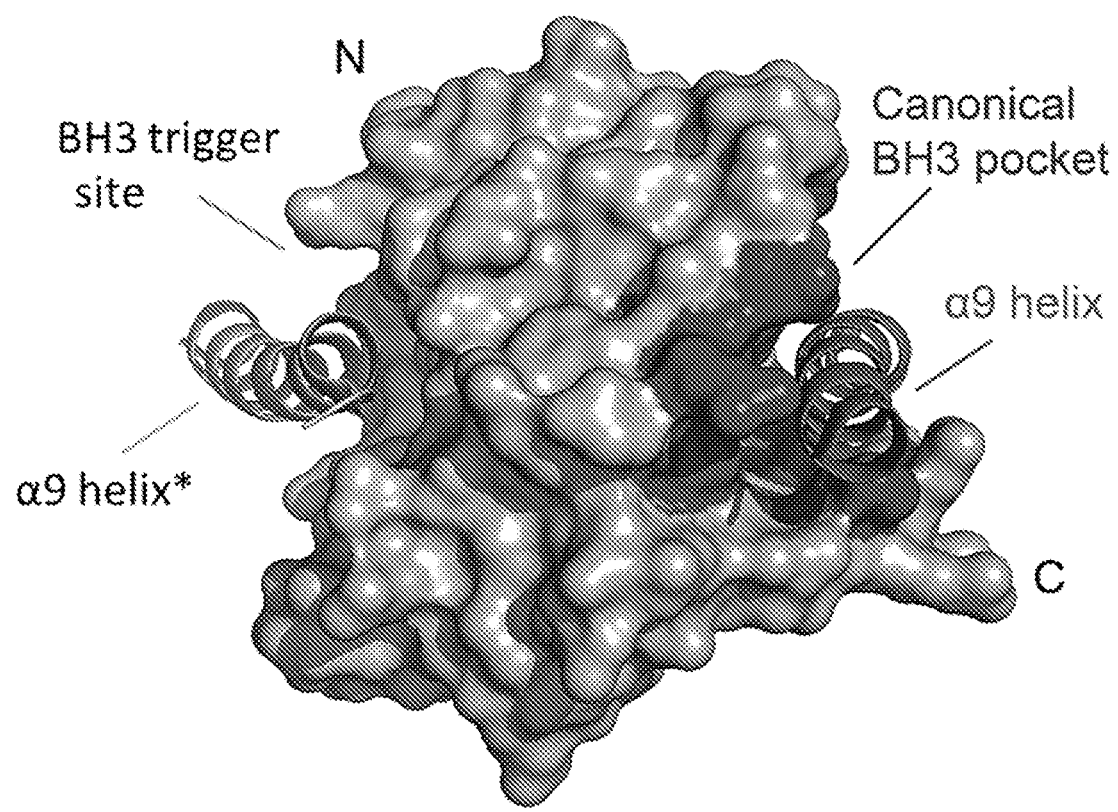
FIG. 12. Structural analysis of the asymmetric BAX dimer crystal structure revealed two novel BAX interaction surfaces forming an autoinhibited dimer conformation. The C-terminal helix α9 of the BAX monomer binds with its solvent inaccessible surface the canonical BH3 pocket (α9 helix on right) and with its solvent accessible surface the BH3 trigger site of another BAX molecule (α9 helix* on left).

Upon BH3 binding to the N-terminal trigger site, the α1-α2 loop is displaced into an open conformation, a conformational change essential for exposure of the 6A7 epitope (residues 12-24) and BAX activation (11,12,17,18) (FIG. 10A). In contrast, in the dimer BAX structure, α9 binds the N-terminal BH3-binding site in an orientation that preserves the conformation of the α1-α2 loop in a closed and inactive conformation (FIG. 10A). Specifically, BIM BH3 binding is mediated by exposed hydrophobic residues of α1 and α6, with conserved hydrophobic residues of BIM BH3 (FIG. 10B, 11A). However in the dimer BAX structure, many of these α1 residues are buried and interact instead with residues of the α1-α2 loop of the same BAX protomer. This generates an alternative hydrophobic cavity formed from the positioning of α1 and the α1-α2 loop, which facilitates the interaction with hydrophobic residues of α9 (FIG. 10C). This closed α1-α2 loop conformation also positions polar and charged residues of the loop to make stabilizing intermolecular hydrogen bonds (FIGS. 10C, 11B). Therefore, these novel interactions within the α1/α6 site and α1-α2 loop stabilize an inactive BAX conformation, block access to the BAX trigger site as well as maintaining helix α9 in place within its own hydrophobic pocket (FIG. 12). These structural insights provide strong evidence that cytosolic BAX forms an autoinhibited dimer that occludes key interactions required for its activation and mitochondrial translocation.

Figure 4A:
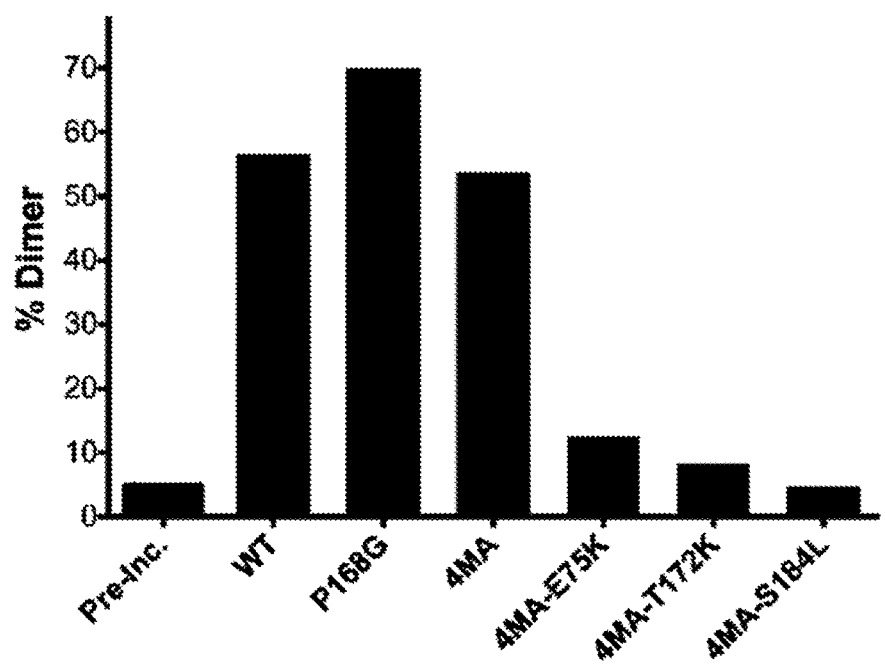
FIG. 4A-4D. Autoinhibited dimer of BAX regulates BAX activation and apoptosis. (A) Dimerization of purified monomeric recombinant BAX WT and mutants was analyzed by SEC and quantified by integration of areas under observed monomer and dimer peaks. (B) Protein lysates of untreated DKO MEFs reconstituted with BAX WT and mutants were subjected to separation of cytosol from mitochondria, followed by SEC using Superdex 200 (HR 10/30). (C) Viability assay of transient transduced DKO MEFs with human BAX WT and mutants as measured by annexin-V binding. P values <0.05 for all mutants compared to BAX WT. (D) BAX WT and BAX P168G cells were treated with 1 μM STS treatment for 6 h; BAX E75K and S184L cells were treated for 3 h due to faster cell death. Cytosolic and mitochondrial fractions were isolated and analyzed by SEC. Data shown in (B) and (D) are representative of three independent experiments and in (A) and (C) are mean±SD from three independent experiments.
Figure 14A:
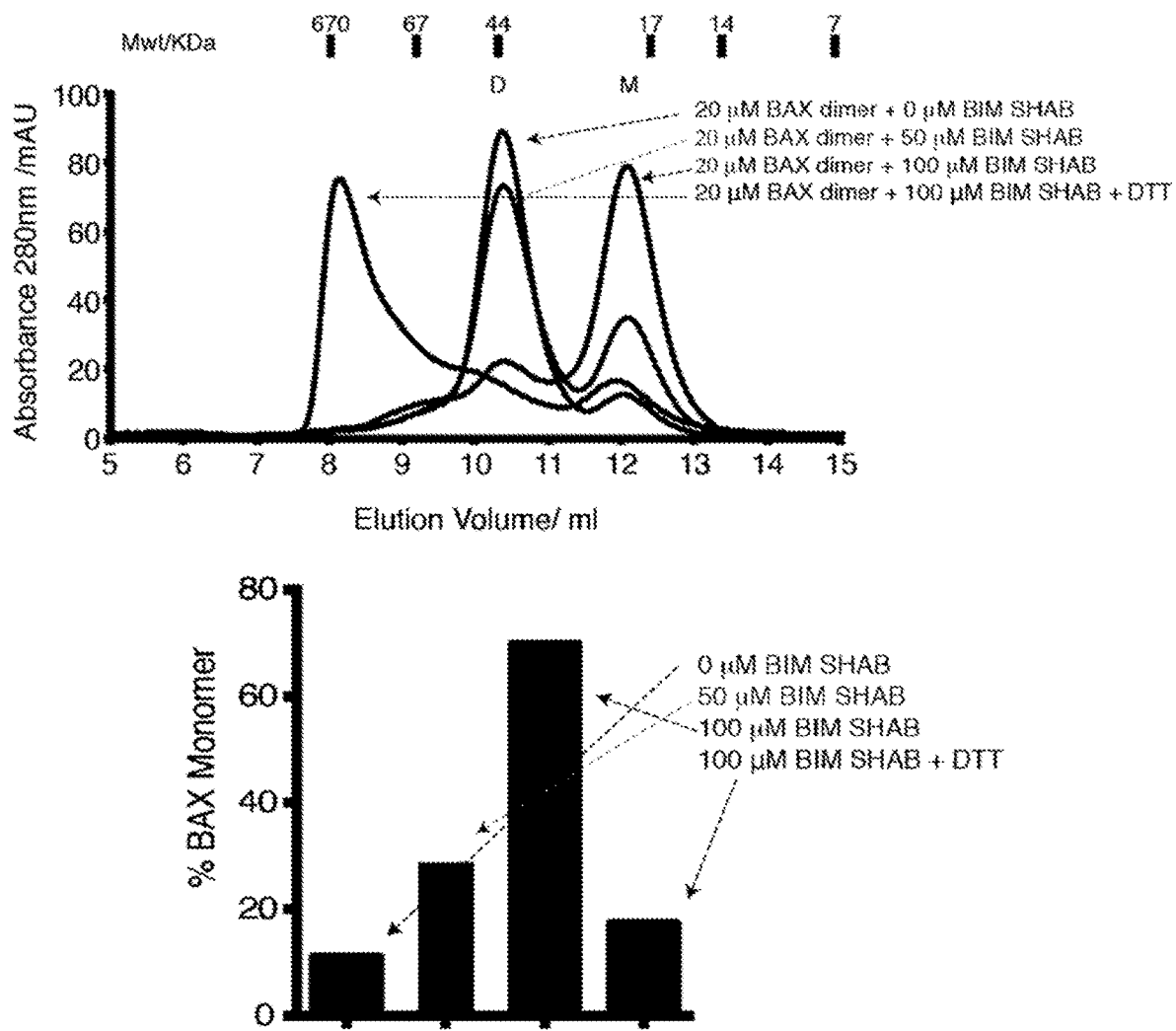
FIG. 14A-14B. The autoinhibited dimeric form of BAX dissociates to BAX monomer before is activated by high doses of the activator BIM SHAB. (A) Inactive BAX 4MA dimer is competed and dissociated to monomer by the trigger site binder, BIM SHAB, at high doses. Upon reduction of the internally crosslinked BAX 4MA mutant using 20 µM DTT, BIM SHAB can activate the 4MA monomer to induce BAX oligomerization. Samples were analyzed by Superdex 75 (HR 10/30) gel filtration chromatography and quantified by integration of areas under observed monomer peaks. Data shown are representative of three independent experiments (B) Liposome permeabilization assay of purified BAX WT dimer and BAX P168G dimer upon treatment with increasing doses of BIM SAHB$_A$. BAX P168G dimer is more resistant to activation by BIM SHAB compared to BAX WT. Notably, the doses that are required for BIM SHAB$_A$ to activate the BAX WT dimer are significantly higher than the dose used to fully activate the BAX WT monomer in FIG. 1. Bar graphs indicate maximum release at 90 min. Data are mean+SD from experiments performed in triplicate and repeated three times.
Figure 14B:
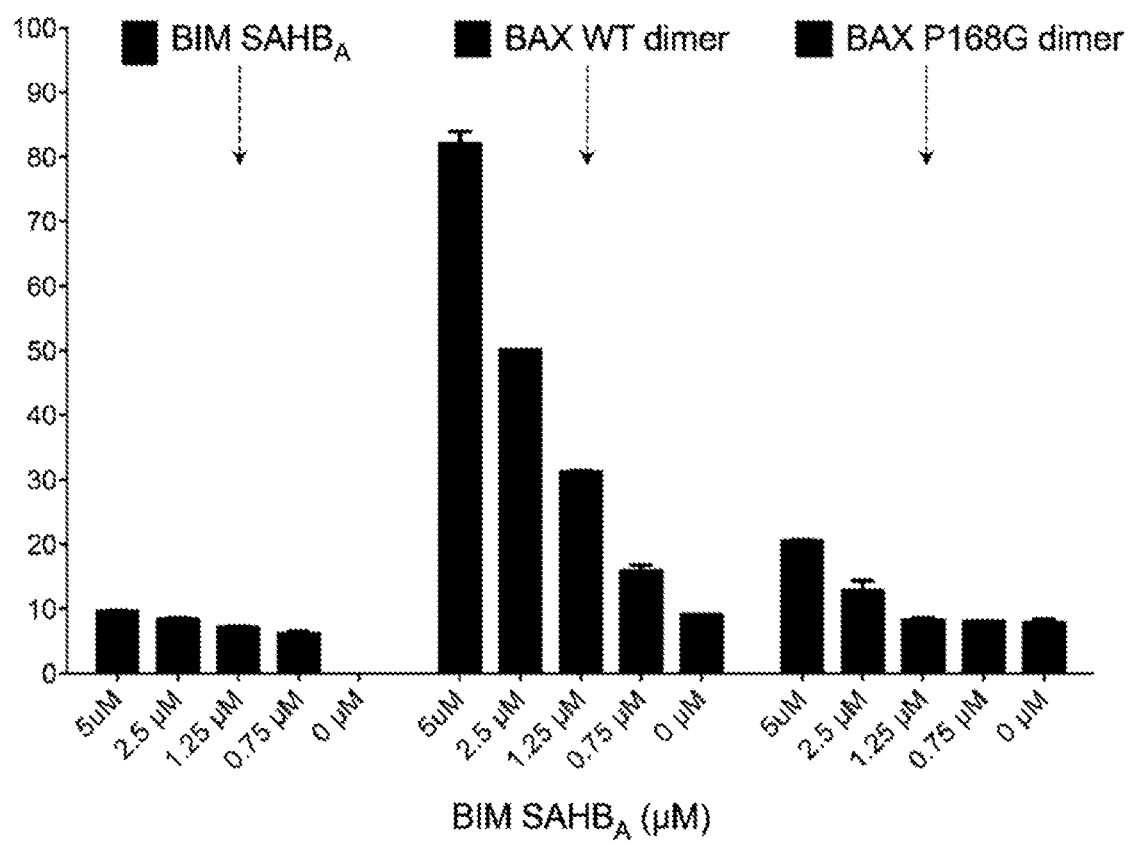

To confirm the dimerization interface in the crystal structure and that the BAX dimer observed in solution is not the domain-swapped dimer previously reported for truncated BAX ΔC21 (13), use was made of an internally cross-linked mutant (C62S, C126S, V121C, I136C) termed 4MA, which is resistant to activation and incapable of forming the domain-swapped dimer as previously reported (13). Expectedly, BAX 4MA retains the ability to form the BAX dimer since these mutations preserve the inactive conformation as in the BAX WT structure (FIG. 4A). Consistent with the dimer crystal structure, mutations in residues forming key interactions at the dimerization interface, E75K and T172K or S184L, which destabilizes the interaction of α9 with the BH3 groove, disrupt dimer formation (FIG. 4A). Next, it was tested whether a N-terminal trigger site binder, BIM SHAB$_A$, can compete and dissociate the dimer. An isolated BAX 4MA dimer was incubated with or without increasing amounts of BIM SHAB$_A$. The results show that BIM SHAB$_A$ at high doses can compete and dissociate the dimer into monomers (FIG. 14A). Furthermore, in the presence of a reducing agent (DTT), which reduces the internally cross-linked BAX 4MA mutant, the BIM SHAB$_A$ can also activate BAX 4MA monomer to induce BAX oligomerization. These biochemical data further validate the autoinhibited dimeric BAX as a mechanism to suppress activation by the BH3-only proteins.

Figure 4B:
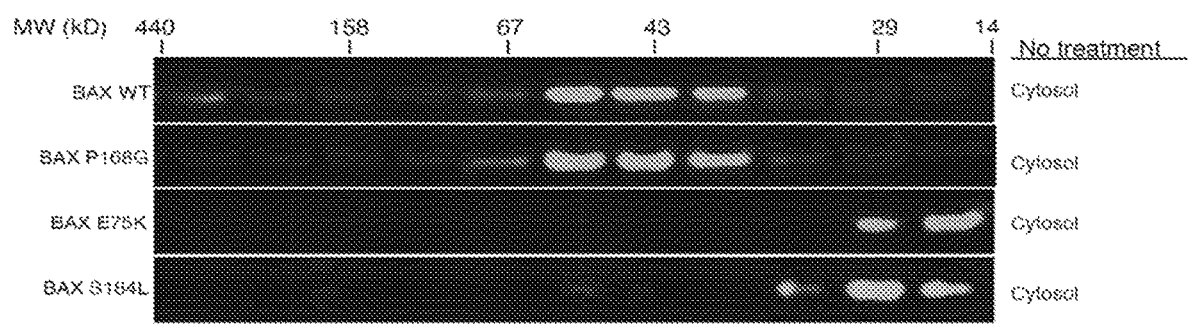
Figure 4C:
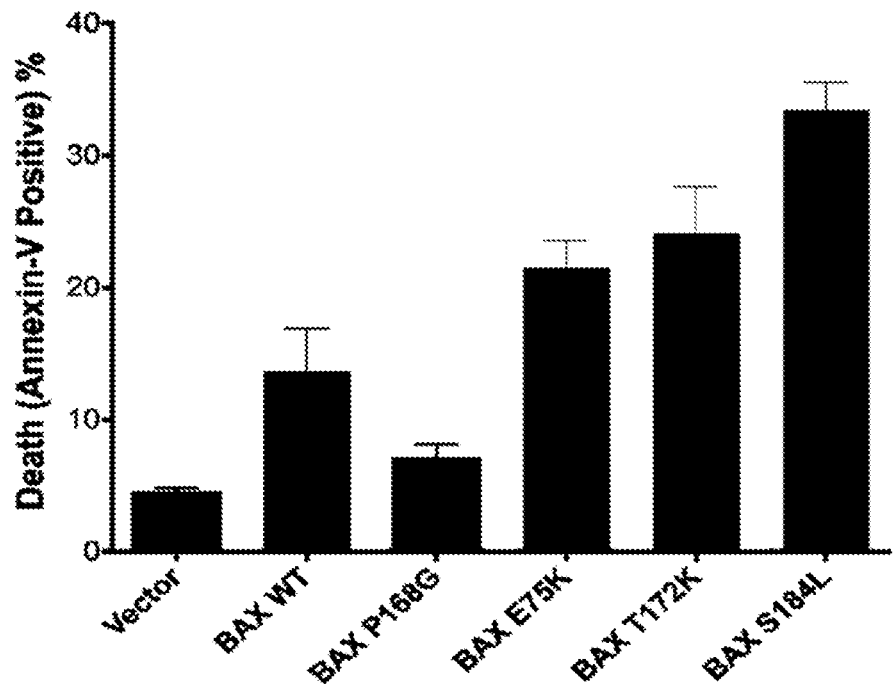
Figure 4D:
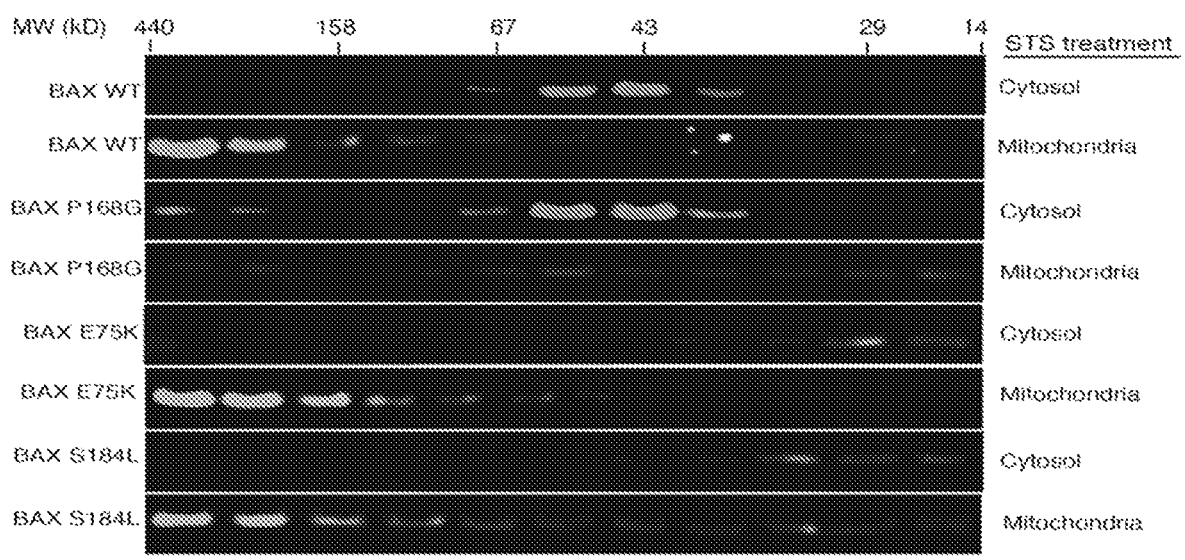

To investigate the physiological role of the BAX dimerization mechanism, an investigation was undertaken of the capacity of BAX WT and mutants to form the autoinhibited dimer and regulate BAX activation. DKO MEFs was reconstituted with BAX WT and mutants at physiological expression levels. P168G mutant forms a more stable autoinhibited dimer than BAX WT (FIG. 4A, FIG. 14B) whereas E75K and S184L mutants disrupt BAX dimerization (FIG. 4A). In agreement with this, both BAX WT and BAX P168G proteins form only dimers in the cytosol; however, the BAX E75K and BAX S184L form monomers in the cytosol (FIG. 4B). Strikingly, constitutive expression of BAX mutants with monomeric BAX showed significantly increased activity in cell death induction compared to BAX WT (FIG. 4C). In contrast, the BAX P168G mutant cells with a more stable cytosolic dimer have impaired activity compared to BAX WT (FIG. 4C). Moreover, upon staurosporine treatment, BAX P168G dimer was more resistant to undergo translocation and oligomerization in the outer mitochondrial membrane compared to BAX WT (FIG. 4D). However, upon staurosporine treatment, monomeric BAX E75K and S184L undergo faster activation and transformation to an oligomer at the outer mitochondrial membrane than the corresponding BAX WT dimer (FIG. 4D). Taken together, the data indicate that cytosolic BAX may switch its conformation from the autoinhibited dimer to a monomer and that monomeric BAX favors faster BAX activation and more potent cell death activity while the dimeric BAX hinders BAX activation and ultimately cell death activity.

Figure 13:
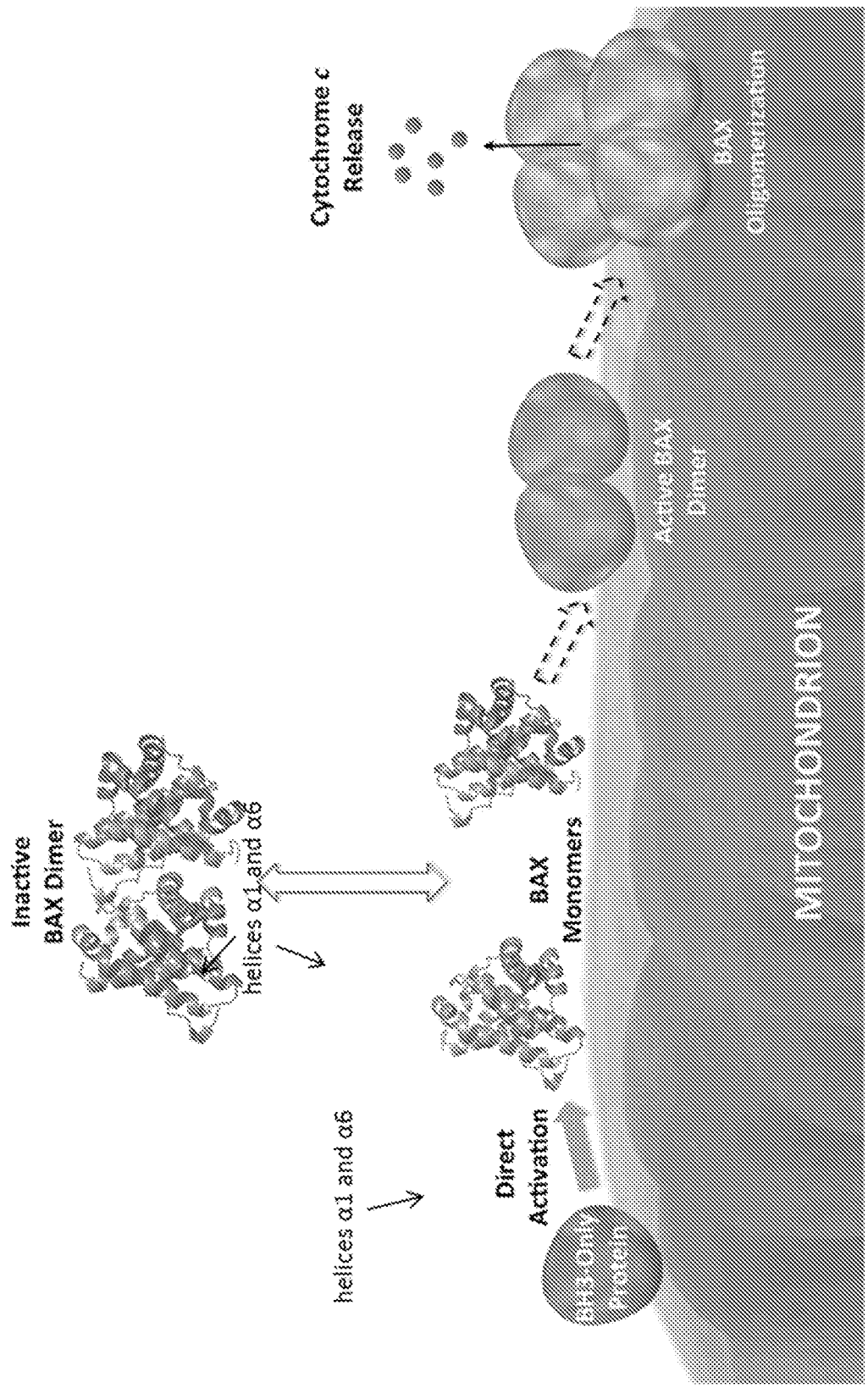
FIG. 13. A model of inactive BAX dimerization that regulates the BAX activation pathway triggered by select BH3-only proteins. Dimerization of inactive and cytosolic BAX provides an off pathway to BAX activation. Direct activation of BAX is initiated by direct interaction with BH3-only proteins and engagement of the trigger site (helices α1 and α6 indicated) of BAX monomers. Conformational change, mitochondrial translocation and autoactivation of BAX proceed and propagate BAX monomers to assemble an active dimer within the outer mitochondrial membrane and a homooligomeric pore to release key apoptogenic factors such as cytochrome c.

During initiation of apoptosis, cytosolic BAX is activated through an interaction of activator BH3-only proteins with the N-terminal trigger site, followed by the N-terminal conformational change and the displacement of α9 from its C-terminal hydrophobic groove, in order to translocate to the mitochondria Moreover, mitochondrial attached BAX with the α9 displaced from its hydrophobic groove undergoes N-terminal conformational change upon further activation by activator BH3-only proteins (13). Regardless of the step of BAX activation, conformational changes at the N-terminal and C-terminal surfaces are required for complete BAX activation leading to membrane permeabilization. The work herein suggests that cytosolic BAX forms an autoinhibited dimer conformation to prevent either the N-terminal or C-terminal conformational change in each protomer and maintain BAX activation under control (FIG. 13). Induction of apoptosis in a cell should require commitment of pro-apoptotic signals (e.g. BH3-only proteins) beyond stochastic fluctuations of their expression levels or active state; therefore, BAX autoinhibition provides a mechanism for blocking BAX activation and preventing unwanted apoptosis. Finally, these structural and functional insights have important implications for the development of pharmacological modulators that engage either the N-terminal site or the C-terminal site to modulate apoptosis in diseases characterized by excessive cell death or survival (2,3).

TABLE 1

Representative dynamic light scattering data of BAX monomer and dimer from size-exclusion chromatography elution peaks.

| BAX | Monomer | Dimer |
| --- | --- | --- |
| Radius/nm | 2.730 | 2.955 |
| Molecular Weight | 22 | 41 |
| Polydispersity/% | 6.8 | 3.2 |
| Mass fraction/% | 97.0 | 98.5 |

TABLE 2

Structural statistics of data collection and refinement.

| Data Collection | | |
| --- | --- | --- |
| Protein | BAX P168G | BAX G67R |
| Beamline | BNL (X29) | APS (23IDD) |
| Space group | P2$_1$ | P2$_1$ |
| Molecule in asymmetric unit | 2 | 2 |
| Resolution (Å) | 50.0-1.90 (1.93-1.90) | 50.0-3.31 (3.31-3.25) |
| Cell Dimensions | | |
| a, b, c (Å) | 63.65, 40.27, 65.30 | 40.58, 65.01, 65.59 |
| α, β, γ (°) | 90.0, 90.01, 90.0 | 90.0, 89.8, 90.0 |
| No. unique observations | 26198 | 4866 |
| Completeness (%) | 98.5 (100) | 89.8 (78.3) |
| R$_{sym}$† | 0.06 (0.65) | 0.13 (0.18) |
| I/σ (I) | 22.1 (2.3) | 26.4 (13.4) |
| Redundancy | 4.6 | 3.0 (2.7) |
| Refinement | | |
| Resolution (Å) | 19.1-1.90 | 46.1-3.30 |
| Reflections | 24766 | 4484 |
| Completeness (%) | 98.6 | 90.1 |
| Number of atoms | 2754 | 2756 |

TABLE 2-continued

Structural statistics of data collection and refinement.

| | | |
|---|---|---|
| Solvent atoms | 124 | n/a |
| $R_{work}$ | 0.20 | 0.22 |
| $R_{free}$ | 0.23 | 0.26 |
| R.m.s.deviations | | |
| Bond lengths (Å) | 0.008 | 0.014 |
| Bond angles (°) | 1.21 | 1.42 |
| B-factors (Å$^2$) | | |
| Overall | 34.7 | 59.1 |
| Main chain | 32.5 | 58.5 |
| Side chain | 36.6 | 59.5 |
| Water | 40.6 | n/a |
| Ramachandran plot (%) | | |
| most favorable region | 98 | 90 |
| additionally allowed region | 2 | 10 |

Numbers in parentheses are for the highest resolution shell.
†$R_{sym} = \Sigma(I - \langle I \rangle)/\Sigma \langle I \rangle$, where I is the intensity measurement for a given refraction and $\langle I \rangle$ is the average intensity for multiple measurements of this refraction.

REFERENCES

1. N. N. Danial, S. J. Korsmeyer, *Cell* 116, 205 (2004).
2. R. W. Johnstone, A. A. Ruefli, S. W. Lowe, *Cell* 108, 153 (2002).
3. D. E. Bredesen, R. V. Rao, P. Mehlen, *Nature* 443, 796 (2006).
4. R. J. Youle, A. Strasser, *Nat. Rev. Mol. Cell. Biol.* 9, 47-59 (2008).
5. J. E. Chipuk, et al., *Mol. Cell.* 37, 299-310, (2010).
6. K. G. Wolter, et al., *J. Cell Biol.* 139, 1281-1292 (1997).
7. I. S. Goping, et al., *J. Cell Biol.* 143, 207-215 (1998).
8. A. Nechushtan, C. L. Smith, Y. T. Hsu, R. J. Youle, *EMBO J.* 18 2330-2341 (1999).
9. M. C. Wei et al., *Science* 292, 727 (2001).
10. S. W. Tait, D. R. Green, *Cold Spring Harb. Perspect. Biol.* 5, (2013).
11. E. Gavathiotis et al., *Nature* 455, 1076 (2008).
12. E. Gavathiotis et al., *Mol. Cell* 40, 481 (2010).
13. P. E. Czabotar, et al., *Cell* 152, 519-531 (2013).
14. G. Lessene, P. E. Czabotar, P. M. Colman, *Nat. Rev. Drug Disc.* 7, 989 (2008).
15. E. Gavathiotis et al., *Nat. Chem. Bio.* 8, 639 (2012).
16. M. Suzuki, R. J. Youle, N. Tjandra, *Cell* 103, 645 (2000).
17. H. Kim et al., *Mol. Cell* 36, 487 (2009).
18. Y. T. Hsu, R. J. Youle, *J. Biol. Chem.* 272, 13829 (1997).
19. Z. Otwinowski, W. Minor, *Methods Enzymol.* 276, 307-326 (1997).
20. Collaborative Computational Project, *Acta Crystallogr D Biol Crystallogr* 50, 760-3, (1994).
21. P. Emsley, K. Cowtan, *Acta Crystallogr D Biol Crystallogr* 60, 2126-2132, (2004).
22. M. D. Winn, G. N. Murshudov, M. Z. Papiz, *Methods Enzymol.* 374, 300-321, (2003).
23. Laskowski, R. A., et al., *Journal of Biomolecular NMR* 8, 477-486 (1996).
24. E. Krissinel, K. Henrick, *J. Mol. Biol.* 372, 774-797. (2007).
25. W. L. DeLano, DeLano Scientific, San Carlos, Calif., USA (2002).
26. Vranken, W. F., et al., *Proteins* 59, 687-696, (2005).

What is claimed is:

1. A method of inhibiting BCL-2-associated X-protein (BAX) comprising contacting BAX with a peptide consisting of a)
    (SEQ ID NO: 12)
TWQTVTIFVAGVLTASLT, b)
    (SEQ ID NO: 13)
TWQTVTIFVAGVLTA, or c)
    (SEQ ID NO: 14)
TWQTVTIFVAGVL, in an amount effective to inhibit BAX.

2. The method of claim 1, wherein BAX is in a living cell and inhibition of BAX inhibits cell death.

3. The method of claim 1, wherein the BAX is in a subject and the peptide is administered to the subject.

4. The method of claim 3, wherein the subject is a human.

5. The method of claim 3, wherein the subject has a disease or disorder associated with premature or unwanted cell death and characterized by abnormal activation, expression or function of BAX.

6. The method of claim 5, wherein the disease or disorder is a cardiovascular disease or disorder, a neurodegenerative or neurological disease or disorder, a liver disease or disorder, a kidney disease or disorder, an immunological disorder, ischemia, infertility, a blood disorder, renal hypoxia, hepatitis, asthma or AIDS.

7. The method of claim 1, wherein the peptide consists of the sequence TWQTVTIFVAGVLTASLT (SEQ ID NO:12).

8. The method of claim 1, wherein the peptide consists of the sequence TWQTVTIFVAGVLTA (SEQ ID NO:13).

9. The method of claim 1, wherein the peptide consists of the sequence TWQTVTIFVAGVL (SEQ ID NO:14).

* * * * *

```
SEQUENCE LISTING

<160> NUMBER OF SEQ ID NOS: 17

<210> SEQ ID NO 1
<211> LENGTH: 192
<212> TYPE: PRT
<213> ORGANISM: Homo sapiens

<400> SEQUENCE: 1

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
        50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
        130                 135                 140

Arg Glu Arg Leu Leu Gly Trp Ile Gln Asp Gln Gly Gly Trp Asp Gly
145                 150                 155                 160
```

```
Leu Leu Ser Tyr Phe Gly Thr Pro Thr Trp Gln Thr Val Thr Ile Phe
            165                 170                 175

Val Ala Gly Val Leu Thr Ala Ser Leu Thr Ile Trp Lys Lys Met Gly
        180                 185                 190

<210> SEQ ID NO 2
<211> LENGTH: 20
<212> TYPE: PRT
<213> ORGANISM: Artificial Sequence
<220> FEATURE:
<223> OTHER INFORMATION: Hydrocarbon-stapled peptide corresponding to
      the BH3 domain of BIM, BIM SAHBA2, where Ser represents the
      non-natural amino acid inserted for olefin metathesis

<400> SEQUENCE: 2

Glu Ile Trp Ile Ala Gln Glu Leu Arg Ser Ile Gly Asp Ser Phe Asn
1               5                   10                  15

Ala Tyr Tyr Ala
            20

<210> SEQ ID NO 3
<211> LENGTH: 192
<212> TYPE: PRT
<213> ORGANISM: Homo sapiens

<400> SEQUENCE: 3

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
            165                 170                 175

Val Ala Gly Val Leu Thr Ala Ser Leu Thr Ile Trp Lys Lys Met Gly
        180                 185                 190

<210> SEQ ID NO 4
<211> LENGTH: 192
<212> TYPE: PRT
<213> ORGANISM: Macaca mulatta

<400> SEQUENCE: 4

Met Asp Gly Ser Gly Glu Gln Pro Arg Gly Gly Gly Pro Thr Ser Ser
1               5                   10                  15
```

```
Glu Gln Ile Met Lys Thr Gly Ala Leu Leu Gln Gly Phe Ile Gln
             20                  25                  30

Asp Arg Ala Gly Arg Met Gly Gly Glu Thr Pro Glu Leu Ala Leu Asp
         35                  40                  45

Pro Val Pro Gln Asp Ala Ser Thr Lys Arg Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Leu
                165                 170                 175

Val Ala Gly Val Leu Thr Ala Ser Leu Thr Ile Trp Lys Lys Met Gly
            180                 185                 190

<210> SEQ ID NO 5
<211> LENGTH: 192
<212> TYPE: PRT
<213> ORGANISM: Bos taurus

<400> SEQUENCE: 5

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
             20                  25                  30

Asp Arg Ala Gly Arg Met Gly Gly Glu Thr Pro Glu Leu Gly Leu Glu
         35                  40                  45

Gln Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                 85                  90                  95

Ala Glu Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190
```

```
<210> SEQ ID NO 6
<211> LENGTH: 192
<212> TYPE: PRT
<213> ORGANISM: Canis lupus fam

<400> SEQUENCE: 6

Met Asp Gly Ser Gly Glu Gln Pro Arg Gly Gly Pro Thr Ser Ser
1               5                   10                  15

Glu Gln Ile Met Lys Thr Gly Ala Leu Leu Gln Gly Phe Ile Gln
                20                  25                  30

Asp Arg Ala Gly Arg Met Gly Gly Glu Thr Pro Glu Leu Pro Leu Glu
            35                  40                  45

Gln Val Pro Gln Asp Ala Ser Thr Lys Lys Leu Ser Glu Cys Leu Lys
50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Glu Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
                180                 185                 190

<210> SEQ ID NO 7
<211> LENGTH: 194
<212> TYPE: PRT
<213> ORGANISM: Rattus norvegic

<400> SEQUENCE: 7

Met Asp Gly Ser Gly Glu Gln Leu Gly Gly Gly Gly Pro Thr Ser Ser
1               5                   10                  15

Glu Gln Phe Met Lys Thr Gly Ala Phe Leu Leu Gln Gly Phe Ile Gln
                20                  25                  30

Asp Arg Ala Glu Arg Met Ala Gly Glu Thr Pro Glu Leu Thr Leu Glu
            35                  40                  45

Gln Pro Pro Gln Asp Ala Ser Thr Lys Lys Leu Ser Glu Cys Leu Arg
50                  55                  60

Arg Ile Gly Asp Glu Leu Asp Asn Asn Met Glu Leu Gln Arg Met Ile
65                  70                  75                  80

Ala Asp Val Asp Thr Asp Ser Pro Arg Glu Val Phe Phe Arg Val Ala
                85                  90                  95

Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
130                 135                 140

Arg Glu Arg Leu Leu Val Trp Ile Gln Asp Gln Gly Gly Gly Trp Glu
```

```
145                 150                 155                 160
Gly Leu Leu Ser Tyr Phe Gly Thr Pro Thr Trp Gln Thr Ile Phe Thr
            165                 170                 175

Ile Phe Val Ala Gly Val Leu Thr Ala Ser Leu Thr Ile Trp Lys Lys
            180                 185                 190

Met Gly

<210> SEQ ID NO 8
<211> LENGTH: 192
<212> TYPE: PRT
<213> ORGANISM: Mus musculus

<400> SEQUENCE: 8

Met Asp Gly Ser Gly Glu Gln Leu Gly Ser Gly Gly Pro Thr Ser Ser
1               5                   10                  15

Glu Gln Ile Met Lys Thr Gly Ala Phe Leu Leu Gln Gly Phe Ile Gln
            20                  25                  30

Asp Arg Ala Gly Arg Met Ala Gly Glu Thr Pro Glu Leu Thr Leu Glu
        35                  40                  45

Gln Pro Pro Gln Asp Ala Ser Thr Lys Lys Leu Ser Glu Cys Leu Arg
    50                  55                  60

Arg Ile Gly Asp Glu Leu Asp Ser Asn Met Glu Leu Gln Arg Met Ile
65                  70                  75                  80

Ala Asp Val Asp Thr Asp Ser Pro Arg Glu Val Phe Phe Arg Val Ala
                85                  90                  95

Ala Asp Met Phe Ala Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Val Trp Ile Gln Asp Gln Gly Gly Trp Glu Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 9
<211> LENGTH: 192
<212> TYPE: PRT
<213> ORGANISM: Pan troglodytes

<400> SEQUENCE: 9

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Arg Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95
```

```
Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 10
<211> LENGTH: 192
<212> TYPE: PRT
<213> ORGANISM: Artificial Sequence
<220> FEATURE:
<223> OTHER INFORMATION: Consensus sequence for SEQ ID NOs:3-9

<400> SEQUENCE: 10

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Thr Pro Glu Leu Ala Leu Glu
        35                  40                  45

Gln Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 11
<211> LENGTH: 24
<212> TYPE: PRT
<213> ORGANISM: Homo sapiens

<400> SEQUENCE: 11

Thr Trp Gln Thr Val Thr Ile Phe Val Ala Gly Val Leu Thr Ala Ser
1               5                   10                  15

Leu Thr Ile Trp Lys Lys Met Gly
            20
```

```
<210> SEQ ID NO 12
<211> LENGTH: 18
<212> TYPE: PRT
<213> ORGANISM: Homo sapiens

<400> SEQUENCE: 12

Thr Trp Gln Thr Val Thr Ile Phe Val Ala Gly Val Leu Thr Ala Ser
1               5                   10                  15

Leu Thr

<210> SEQ ID NO 13
<211> LENGTH: 15
<212> TYPE: PRT
<213> ORGANISM: Homo sapiens

<400> SEQUENCE: 13

Thr Trp Gln Thr Val Thr Ile Phe Val Ala Gly Val Leu Thr Ala
1               5                   10                  15

<210> SEQ ID NO 14
<211> LENGTH: 13
<212> TYPE: PRT
<213> ORGANISM: Homo sapiens

<400> SEQUENCE: 14

Thr Trp Gln Thr Val Thr Ile Phe Val Ala Gly Val Leu
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Peptide that interacts with the N-terminal
      binding site of BAX
<220> FEATURE:
<221> NAME/KEY: MISC_FEATURE
<222> LOCATION: (2)..(2)
<223> OTHER INFORMATION: X at any position can independently be any
      amino acid or unnatural amino acid or non-naturally occurring
      chemically modified amino acid
<220> FEATURE:
<221> NAME/KEY: MISC_FEATURE
<222> LOCATION: (5)..(6)
<223> OTHER INFORMATION: X at any position can independently be any
      amino acid or unnatural amino acid or non-naturally occurring
      chemically modified amino acid
<220> FEATURE:
<221> NAME/KEY: MISC_FEATURE
<222> LOCATION: (9)..(9)
<223> OTHER INFORMATION: X at any position can independently be any
      amino acid or unnatural amino acid or non-naturally occurring
      chemically modified amino acid

<400> SEQUENCE: 15

Thr Xaa Gln Thr Xaa Xaa Ile Phe Xaa Ala Gly
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Peptide that interacts with the N-terminal
      binding site of BAX
<220> FEATURE:
<221> NAME/KEY: MISC_FEATURE
<222> LOCATION: (2)..(2)
<223> OTHER INFORMATION: X at any position can independently be any
``` amino acid or unnatural amino acid or non-naturally occurring
     chemically modified amino acid
<220> FEATURE:
<221> NAME/KEY: MISC_FEATURE
<222> LOCATION: (5)..(6)
<223> OTHER INFORMATION: X at any position can independently be any
     amino acid or unnatural amino acid or non-naturally occurring
     chemically modified amino acid
<220> FEATURE:
<221> NAME/KEY: MISC_FEATURE
<222> LOCATION: (9)..(9)
<223> OTHER INFORMATION: X at any position can independently be any
     amino acid or unnatural amino acid or non-naturally occurring
     chemically modified amino acid
<220> FEATURE:
<221> NAME/KEY: MISC_FEATURE
<222> LOCATION: (13)..(13)
<223> OTHER INFORMATION: X at any position can independently be any
     amino acid or unnatural amino acid or non-naturally occurring
     chemically modified amino acid

<400> SEQUENCE: 16

Thr Xaa Gln Thr Xaa Xaa Ile Phe Xaa Ala Gly Val Xaa Thr Ala
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: Peptide that interacts with the N-terminal
     binding site of BAX
<220> FEATURE:
<221> NAME/KEY: MISC_FEATURE
<222> LOCATION: (1)..(1)
<223> OTHER INFORMATION: X is threonine or a conserved amino acid, or
     unnatural amino acid or non-naturally occurring chemically
     modified amino acid
<220> FEATURE:
<221> NAME/KEY: MISC_FEATURE
<222> LOCATION: (2)..(2)
<223> OTHER INFORMATION: X is any amino acid, or natural or
     non-naturally occurring chemically modified amino acid
<220> FEATURE:
<221> NAME/KEY: MISC_FEATURE
<222> LOCATION: (3)..(3)
<223> OTHER INFORMATION: X is glutamine or a conserved residue or
     unnatural amino acid or non-naturally occurring chemically
     modified amino acid
<220> FEATURE:
<221> NAME/KEY: MISC_FEATURE
<222> LOCATION: (4)..(4)
<223> OTHER INFORMATION: X is threonine or a conserved amino acid, or
     unnatural amino acid or non-naturally occurring chemically
     modified amino acid
<220> FEATURE:
<221> NAME/KEY: MISC_FEATURE
<222> LOCATION: (5)..(6)
<223> OTHER INFORMATION: X is independently any amino acid, or natural
     or non-naturally occurring chemically modified amino acid
<220> FEATURE:
<221> NAME/KEY: MISC_FEATURE
<222> LOCATION: (7)..(7)
<223> OTHER INFORMATION: X is isoleucine or a conserved amino acid, or
     unnatural amino acid or non-naturally occurring chemically
     modified amino acid
<220> FEATURE:
<221> NAME/KEY: MISC_FEATURE
<222> LOCATION: (8)..(8)
<223> OTHER INFORMATION: X is phenylalanine or a conserved amino acid,
     or unnatural amino acid or non-naturally occurring chemically
     modified amino acid
<220> FEATURE:
<221> NAME/KEY: MISC_FEATURE
<222> LOCATION: (9)..(9)
<223> OTHER INFORMATION: X is any amino acid, or natural or
     non-naturally occurring chemically modified amino acid

```
<220> FEATURE:
<221> NAME/KEY: MISC_FEATURE
<222> LOCATION: (10)..(10)
<223> OTHER INFORMATION: X is alanine or a conserved amino acid, or
      unnatural amino acid or non-naturally occurring chemically
      modified amino acid,
<220> FEATURE:
<221> NAME/KEY: MISC_FEATURE
<222> LOCATION: (11)..(11)
<223> OTHER INFORMATION: X is glycine or a conserved amino acid, or
      unnatural amino acid or non-naturally occurring chemically
      modified amino acid

<400> SEQUENCE: 17

Xaa Xaa Xaa Xaa Xaa Xaa Xaa Xaa Xaa Xaa Xaa
1               5                   10
```